(12) United States Patent
Rushbrooke et al.

(10) Patent No.: US 6,263,095 B1
(45) Date of Patent: Jul. 17, 2001

(54) IMAGING METHOD AND APPARATUS

(75) Inventors: John Gordon Rushbrooke; Claire Elizabeth Hooper, both of Cambridge; William Wray Neale, deceased, late of Cambridge, by Bam Neale, personal representative; Richard Eric Ansorge, Cambridge, all of (GB)

(73) Assignee: Cambridge, Imaging Ltd., Cambridge (GB)

( * ) Notice: Subject to any disclaimer, the term of this patent is extended or adjusted under 35 U.S.C. 154(b) by 0 days.

(21) Appl. No.: 09/294,709

(22) Filed: Apr. 19, 1999

Related U.S. Application Data

(63) Continuation-in-part of application No. 08/817,813, filed as application No. PCT/GB95/02436 on Oct. 18, 1995, now abandoned.

(30) Foreign Application Priority Data

| Oct. 20, 1994 | (GB) | ................................................. 9421510 |
| Apr. 18, 1995 | (GB) | ................................................. 9507830 |
| Jun. 8, 1999 | (GB) | ................................................. 9511666 |

(51) Int. Cl.$^7$ .................................................. G06K 2/00

(52) U.S. Cl. .......................... 382/128; 382/129; 382/172; 382/195; 382/203; 435/5; 435/6; 436/516; 436/518; 436/172; 364/555

(58) Field of Search .............. 435/5, 6; 436/516, 436/518, 172; 364/555; 382/128, 129, 172, 195, 203

(56) References Cited

U.S. PATENT DOCUMENTS 4,979,221 * 12/1990 Perryman et al. ....................... 382/1

FOREIGN PATENT DOCUMENTS

0532271 * 12/1993 (JP) .

* cited by examiner

*Primary Examiner*—Jeffrey Stucker
(74) *Attorney, Agent, or Firm*—Lee, Mann, Smith, McWilliams, Sweeney and Ohlson.

(57) ABSTRACT

A method of detecting the presence and position of labelled material in a sample in which the labelled material either gives off light or can be stimulated to do so. The sample is imaged onto a CCD array which is scanned following each exposure. A cooled CCD camera or an image intensified CCD camera may be used. Measurements are performed on the data signals so obtained, to identify clusters of data values from adjacent regions of the CCD array caused by light incident on those regions. The measured signal values are compared with at least one threshold so as to distinguish clusters resulting from light emitting regions of labelled material from the remainder of the sample and the centroid of each light produced cluster of data values is computed with reference to the camera array, and a signal value corresponding to the centroid coordinates is stored in a memory together with the centroid coordinates of any other light produced clusters identified during the same interrogation. The coordinates from each of a succession of interrogations of the same sample may be stored in an accumulation store to enable a list of the recorded light emissions and/or display of events, to be produced by reading out the store. Apparatus for performing this method is also described.

37 Claims, 15 Drawing Sheets

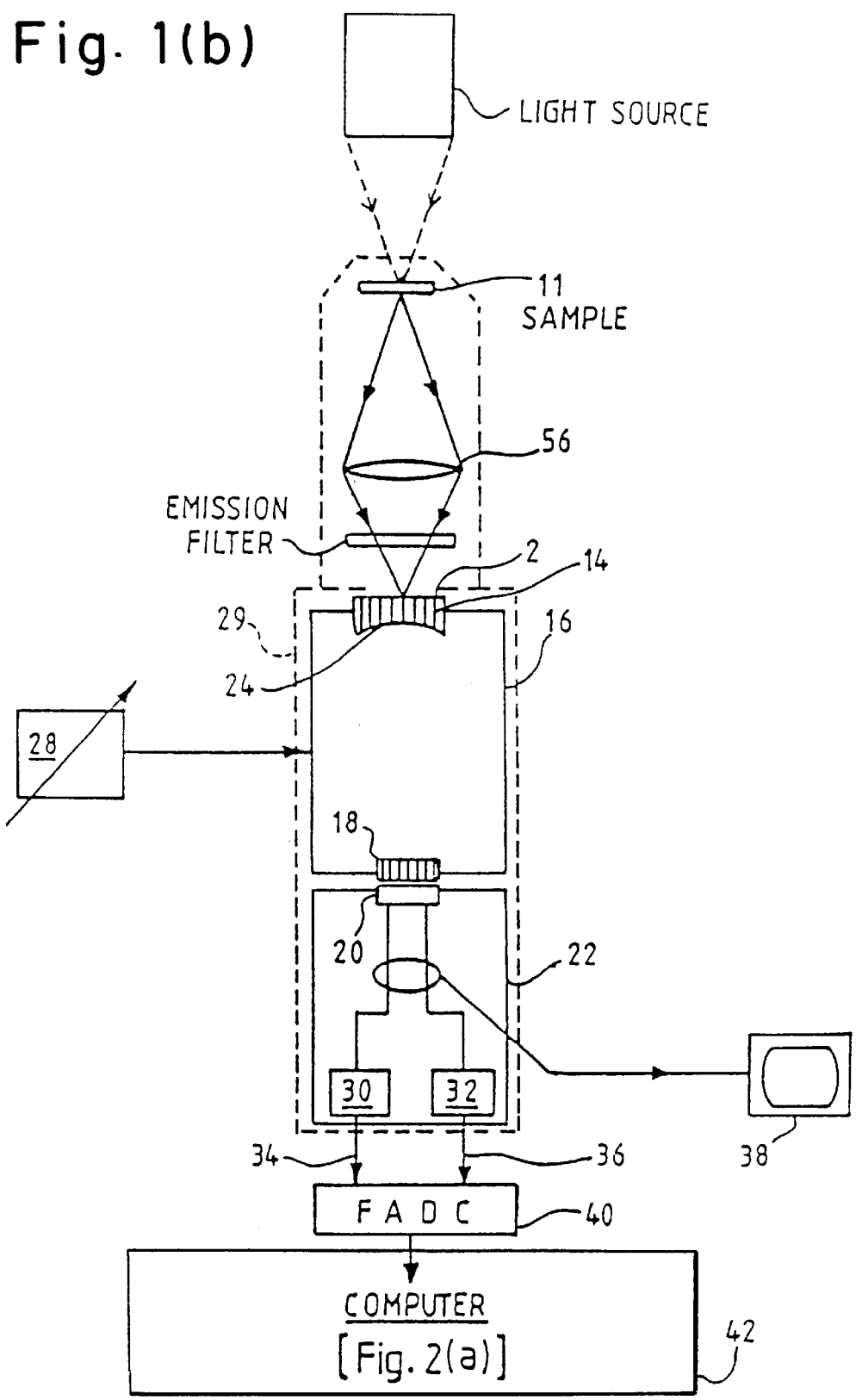

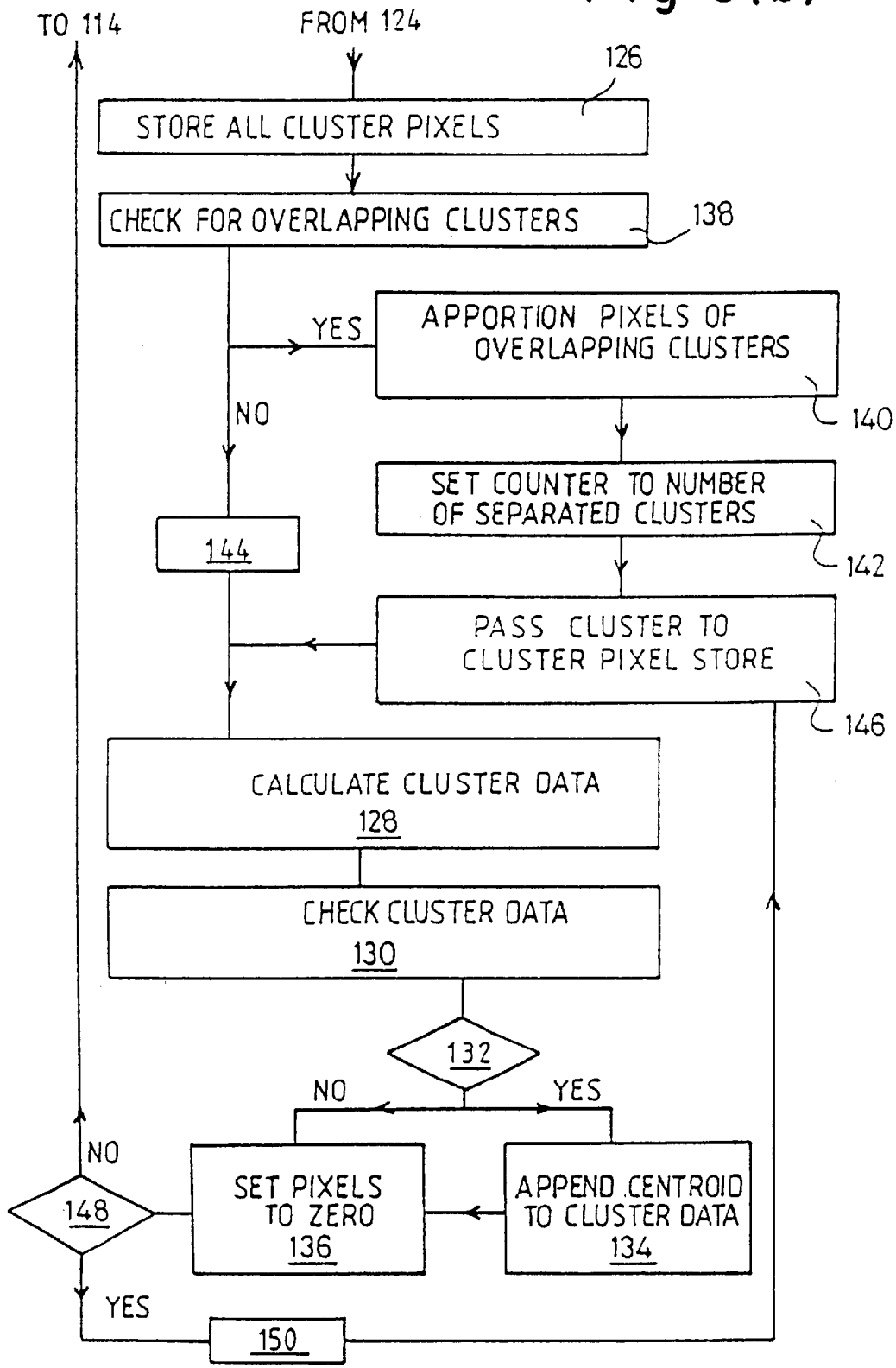

IMAGING METHOD AND APPARATUS

RELATED APPLICATION

This application is a continuation-in-part of U.S. patent application Ser. No. 08/817,813, filed Jun. 13, 1997 now abandoned, which is a national stage application of PCT/GB95/02436, filed Oct. 18, 1995.

FIELD OF INVENTION

This invention concerns methods and apparatus for detecting the presence and position of materials labelled with a substance which emits radiation in the visible range of the electromagnetic spectrum on a sample.

The invention is of application in the field of diagnostics and analysis and for performing measurements and analysis on labelled immunoassays, tissue sections, microbiological specimens, cellular specimens, cellular monolayers, reporter genes, DNA and/or protein gels and blots.

U.S. Pat. No. 4,979,221 Perryman disclosed a photon event detection system in which a regular pattern or array of pixels is used as the window within which photon events on a CCD array are to be investigated. The system is suited to the application for which it was designed where in general it could be known in advance that a 3×3 array of pixels would always in at least one position, encompass all the pixels attributable to an event of interest. That is not the case with chemiluminescence arrays, labelled immonuassays and other low light level emitting specimens such as listed above particularly where the affected pixels can be spaced over irregularly shaped areas encompassing far more than a 3×3 matrix of pixels. It is an object of the invention to provide a pixel investigation technique which can accommodate irregularly shaped regions of affected pixels in a CCD array.

The invention is also of particular application to diagnostic analysis of samples in which the concentration of light emitting material and therefore the quantity of light from different regions of the sample can vary considerably from one region to another in the filed of view.

It is an object of the present invention to provide an improved method and apparatus by which light from a plurality of different points in a sample can be detected and mapped in two dimensions and quantified.

It is a further object to provide a method and apparatus as aforesaid which is nevertheless capable of detecting and mapping points from which light is being emitted at low levels and from such points when present in the same sample as points from which considerably higher levels of light are being emitted, due to events which may have nothing to do with the sample, such as ion events in an image intensified CCD camera. In this connection, the system described in U.S. Pat. No. 4,979,221 Perryman does not allow such events to be distinguished.

DESCRIPTION OF THE INVENTION

According to one aspect of the present inventor a method of detecting the presence and position of labelled material in a sample in which the labelled material either gives off light or can be stimulated to do so comprises the steps of repetitively imaging the sample onto a CCD camera, scanning the camera CCD array and interrogating the charge pattern thereon following each exposure, performing measurements on the data signals obtained to identify clusters of data values from adjacent regions of the array caused by light emitted from the sample onto those regions and comparing the measurements with at least one threshold so as to distinguish clusters resulting from light emitting regions of labelled material from the remainder of the sample, and computing the centroid of each light produced cluster of data values so identified with reference to the camera array, and storing the centroid coordinates in a memory together with the centroid coordinates of any other light produced clusters identified during the same interrogation.

The method may include the further step of storing the coordinates from each of a succession of interrogations of the same sample in an accumulation store, which can be read out to give a list of the recorded light emissions and/or used to produce a display of the events which may also be superimposed on an outline of the sample.

According to another aspect of the present invention a method of detecting the presence and position of light emitting labelled material in an area of sample comprises the steps of:

1. imaging the sample onto a CCD camera,
2. repetitively scanning the CCD array of the camera, each scan corresponding to an interrogation of the charge pattern on the array and being preceded by an exposure period and followed by a resetting step, which initiates the beginning of the next following exposure period,
3. generating during each interrogation data signals whose values described the charge pattern on the array,
4. performing measurements on the data signals to identify clusters of data values from adjacent regions of the array indicative that photon emission from the sample has impinged thereon, and
5. identifying a center position of each identified cluster of such data values and storing the center coordinates in a memory together with the centre coordinates of any other identified clusters occurring during the same interrogation.

Preferably the data signal values generated for each interrogation are stored and subsequently read out by computing and data processing means for performing the said measurements thereon.

Preferably coordinates from each of a succession of interrogations of the same sample are stored in an accumulation store.

The invention also lies in the further step of reading out the stored coordinates and producing a list thereof.

The method also lies in the further step of operating a visual display system so as to reproduce therein the scanned area of the CCD array and modulating the light producing element of the display system so as to generate visually distinguishable features in the display at positions defined by the stored coordinates.

Either a cooled CCD camera or an image intensified CCD camera may be employed.

Where an image intensified CCD camera is employed, a so-called first generation image intensifier is preferred.

Noise reduction can be enhanced if a low noise material is selected for the photocathode of the image intensifier.

Preferably a first generation image intensifier is selected having a low noise bi-alkali material photocathode.

CCD Camera operation

The CCD camera may be operated in so-called "inverted mode" so that contributions to background from fluctuations in thermal noise in tis CCD array (so called "shot noise"), at room temperatures, can be reduced, but in any case is cooled, typically cryogenically.

To reduce dead time, the duration of each interrogation of the charge pattern of the CCD array and the associated resetting of the CCD array, is preferably as short as possible and will normally be much shorter than the duration of the preceding exposure period.

According to a preferred feature of the method, the addressing of the CCD array is organized so as to define a plurality of sub-regions which together make up the optically sensitive region of the camera array. The quantity of photon energy incident on each sub-region during an exposure period determines the charge to be found on that sub-region during the following interrogation, so that an electrical signal indicative of the photon energy incident on each sub-region can by obtained and stored as an electrical information signal for each sub-region.

Display of CCD camera signal

For display purposes a light producing element of a scanning display system may be modulated by the said electrical information signal obtainable for the interrogation of the CCD array, so as to generate a visual difference between one part of the display and another depending on the level of photon activity on the corresponding sub-regions of the CCD array during the preceding exposure period.

If instead the display system is modulated by signals obtained by repeatedly reading out the coordinate accumulation store previously referred to, the display will present a continually updated picture of the positions from which light has been detected in the sample.

A threshold may be applied to the information signals so that in the simplest case the modulation is two-state and sub-regions which have received photon energy greater than a value for example K, are displayed in one colour and all other sub-regions are displayed in a contrasting colour. Those regions displayed in the said one colour will indicate that in those regions a greater level of photon activity has occurred from the corresponding regions in the sample since the amount of light incident on the CCD is linked to the photon energy incident out eh different regions of the photocathode.

Processing of CCD output signals

The sub-region related information signals may be employed to produce a list of coordinates at which events have occurred.

By storing all such event coordinates for each interrogation, the list will contain an accumulation of the events relating to the light emissions over a period of time and which is continually updated from each interrogation of the CCD array.

An analysis of the information signals from one interrogation or from a succession of interrogations, will reveal the size and shape and position of those regions of the sample containing the light emitting material.

System sensitivity

The sensitivity of the imaging system (and therefore overall signal processing and image analysing system) may be enhanced by optically coupling the sample to the photocathode of the image intensifier by means of a fiber optic couple plate, which advantageously may alter in cross-section from the face coupled to the sample, to the face which couples to the CCD camera, the latter being commensurate with the area of the CCD input window and the former being commensurate with the area of the sample.

If the area of the sample is greater than the area of the CCD input window, and an appropriate fiber optic plate is selected, demagnification is achieved and a lager area of a sample (or a number of different samples simultaneously) can be viewed by the one CCD camera.

If a fiber optic plate is selected whose area increases between the sample and CCD camera (the area of the latter still being commensurate with the camera input), the latter will effectively view a magnified image of the sample, the magnification being determined by the ratio of the two areas.

By using tapering (converging or diverging) fiber optic plates, magnification or demagnification is achievable to the same extent as would be possible by using a lens system but with significantly less light loss. At low light levels this is of major importance.

Elimination of data relating to unwanted events, noise, etc.

As a general principal only groups of signals from contiguous sub-regions are retained for subsequent processing and analysis by means of thresholding.

Determination of cluster centre

Having identified a group or cluster as a possible candidate for classification as a signal photoelectron event, the position coordinates of a point within the area encompassing the sub-regions from which the radiation appears to have originated must be identified, as being the best estimate of the position of the point in the sample from which the light has been emitted.

The centroid of the area defined by the group may be used as the best estimate of that position. The centroid position coordinates may be computed to any desired level of accuracy and typically floating point coordinates are used so that the resolution is not limited to the resolution of the sub-regions.

Ion events

In general, ion events arising when an image intensifier is employed, normally lead to signals of magnitude larger than those due to single photoelectrons, and where possible these ion event signals must be identified and removed.

According to the invention this may be achieved by applying appropriate thresholding algorithms to the signals from each identified group of sub-regions found during each interrogation and performing the identification in real time.

Identification can be achieved by noting the total charge on the CCD sub-regions of a group pertaining to an event, and noting the size of the group (for example the nuimber of sub-regions within the group). Using both pieces of information, it is possible to determine the nature of the originating event. The relevant group can then by identified as one arising from a light emission in the sample, and its position coordinates stored and/or displayed, or can be identified as one arising from an ion event, in which case it is rejected.

It has also been found beneficial to use a lower operating voltage for the image intensifier than would normally be employed, since in the case of a first generation image intensifier the effect is to reduce the size and number of internal ion events in the intensifier without affecting the sensitivity to photon events at the photocathode from the sample.

Particular applications of the invention (1) Single identifier labelling

The method of the invention permits analysis of the distribution of a labelling material across a sample, both visually and electronically by computational analysis of electrical signals descriptive of the said distribution. It may be used for example to determine drug take-up tissue by and/or cells, and DNA, RNA or protein hybridisation.

Since in practice light from the sample will cause charge to be deposited over more than one addressable region of the CCD camera array, the method according to the invention preferably includes the step of centroid signals from a group of such sub-regions, identified as being linked to a signal emission, so as to estimate the position in the sample of the point from which the light has emanated, and which caused the charge distribution concerned, and identifying that position as being the point of interest, and storing the coordinates of that position for subsequent mapping of labelling material relative to the sample.

(2) Multiple identifier labelling

If the presence and position of two or more differently labelled material in the sample is required to be determined, then materials giving off different wavelength light can be used to enable the different substances to be identified using for example optical filtering before the CCD, and the presence of the two or more different materials in the sample can be checked by identifying clusters as before and storing with each cluster not only the center coordinates by also an indication as to the wavelength of the light therefrom. The distribution of two or more different materials in the sample can of course only be analysed if the range of wavelengths of the light from the one material is sufficiently different from the range of wavelengths from the other.

The invention also lies in a method of determining the distribution of a first material in a base material, such as the distribution of a drug within organ tissue, comprising the steps of:

(1) labelling the first material with a light emitting substance, (2) exposing the base material to the first material (which may be in the form of a thin slice thereof), in manner such that take-up of the first material by the base can be expected, and if not in the from of a thin slice removing from the said base material a thin slice thereof after said exposure, (3) coupling the thin slice of exposed base material with a CCD camera input window, (4) imaging the photocathode output onto a CCD array, (5) establishing a uniform charge pattern on the CCD array at the beginning of each of a succession of exposure periods, at the end of each of which the array is interrogated, and the charge pattern thereon is read out before reinstating the uniform charge pattern, (6) converting the read-out electrical charge patterns into electrical signals indicative of the variation in charge over the array, (7) position-relating the electrical signals to the array, to permit the presence and position of sites of photon activity from the image intensifier (and therefore the photon of a light emitting material in the sample area) to be identified from the said electrical signals, (8) determining from an analysis of the electrical signals background noise events produced within the CCD array, and excluding therefrom signals relating to all such events, and (9) storing coordinates of points approximating to the center of each site for which electrical signals remain with reference to their position in the CCD array, as the coordinates of points from which light has been emitted.

A cooled CCD camera or an image intensified CCD camera may be employed.

The signals derived from the stored central point coordinates may be used to control a visual display device for displaying the points in a two-dimensional display.

The centre points determined during each interrogation of the CCD array may be accumulated in an accumulation store and the two-dimensional display is updated from the store on a regular basis so as to indicate all points for which photon activity is attributable from a given sample.

Definition of sub-regions of CCD array

A CCD array comprises a large number of capacitive junctions in which electrical charge is generated therein in the presence of photon energy. The greater the number of photons incident on the capacitive junction the greater the generation in charge. The capacitive junctions are closely packed so that in an area of the order of 1 $cm^2$, there may be 300,000 pixels uniformly distributed over the area. The CCD array is initialized by ensuring a uniform electrical charge in each of the junctions. The array is then exposed to light and at the end of a given exposure period, the charge generated in each of the junctions is determined by addressing each of the junctions and reading out the charge remaining therein. Various techniques have been developed to address the junctions at high speed so that the time required to read out the signal is very small and by using a so-called dual mode CCD array, the dead-time associated with the read out of the information can be reduced very considerably by blanking half of the junctions and transferring the charge from the other half into the blanked junctions which can then be read out while the original junctions are initialised and exposed once again. In this way relatively high repetition rates can be achieved with little or no dead time.

Unless colour discrimination at the CCD is required, the light incident on the CCD array can be thought of as monochromatic and only the luminance content of the image falling in the CCD array needs to be considered. In inverted mode operation of a CCD this can vary from zero photons during the exposure to sufficient photons to completely saturate the junction with charge. These two extremes correspond to black and white saturation and the ability to measure the charge in between those two extremes determines the grey level resolution capability of the CCD array. Typically up to 256 grey levels between black and white can be measured but where low light levels are concerned and the charge reduction even from a relatively bright event will only cause a minimal change in the charge per junction, the 256 grey level slicing may be applied over a smaller dynamic range of charge variation thereby ensuring the same grey level resolution albeit over a smaller range of grey levels, between zero photons and the few photons expected per the event and which are likely to arrive at the CCD array.

Greater or lesser quantization of the charge may of course be utilised, the figure of 256 merely being used as an example.

Resolution in the XY direction is limited to the size and spacing of the junctions and in the limit, the smallest resolvable point is each junction. When displaying a picture by modulating for example a CRT display so that the scanning spot is caused to produce more or less light at each point in the display in dependence upon the quantised charge signal from the CCD for the corresponding points in the CCD array, the resolution in the final display (assuming that the scanning spot size relative to the display area is no larger in proportion than the area of a juction to the overall area of the CCD array) will be limited by the junction size and spacing in the CCD array. Conventionally the points making up the overall CRT display are referred to as pixels and in that event the array junctions can also be thought of as being pixels since there is a one to one relationship. Alternatively groups of junctions may be linked together and read simultaneously so that each pixel in fact corresponds to a group of junctions, not a single junction in the CCD array.

In the following analysis, the term pixel is employed rather than sub-region. It is to be understood that the reference to pixels can mean individual junctions in the CCD array or groups of junctions for the reason given above. However where the display resolution is greater than the resolution possible in the CCD the positions of points whose coordinates have been computed to floating point accuracy from the data obtained from the CCD the positions of these points in the display will be displayed to the greater accuracy possible as a consequence of the higher resolution in the display.

Dark level variation and correction

Whether individual junctions or groups of junctions are addressed as pixels, the recharge per pixel during read-out of the array (even when the device has not been exposed to any light), will be found to vary from one region of the array to another. This variation is sometimes referred to as dark level variation and is similar to the problem of so-called "shading" in vidicon television cameras.

The variation can be determined at the time of manufacture and a look-up table provided of correcting signals which can be obtained by synchronously reading out the look-up table during subsequent addressing of the CCD array.

The correcting signals may be applied as an offset to the digital values for each pixel during interrogation of the CCD array or may be applied as an offset to a threshold value with which the pixel digital values are to be compared. The net effect is the same.

The dark-level look-up table values can be recalibrated at any time by simply exposing the CCD array to no illumination and reading out the pixel value and replacing the signals in the look-up table with signals derived from the new pixel signals obtained from the recalibration read-out.

Since CCD arrays for use in methods and apparatus embodying the present invention will often be involved with low light levels, dark level correction will be assumed to be provided for the camera.

Cluster identification and centroid labelling algorithms

The algorithms by which events can be identified and distinguished from background noise signals, will now be described in more detail.

For any cluster of pixels belonging to an event identified as described above, there is available from any one interrogation the individual count $q_i$, for each pixel i. The dark level correction for pixel i, namely b, can be read from a dark level look-up table file obtained as described, as a series of acceptance criteria can be applied to the information available from the interrogation assuming a known pixel density on and known size of the CCD.

1. The number of pixels in a cluster N must be between an upper threshold and a lower threshold for the cluster to be accepted as candidate for consideration as a light emitting point. The upper limit serves the purpose of eliminating from the candidate list, clusters which retest from anomalous events producing large quantities of light. The lower limit serves to remove events arising from phenomena which only affect individual or small numbers of pixels, such as for example events caused by cosmic rays passing through, or from fluctuations in dark-level generation in the silicon of the CCD, such as an image intensifier system, when used.

2. The excess of photon activity descriptive pixel signals above a chosen lower limit (which may have to be as low as the dark level value for each pixel), can be added for all pixels in a cluster to make a sum S. By requiring S to be within a chosen range, it is possible to eliminate clusters due to large unwanted events such as can occur on an image intensifier.

3. In general, such events can be eliminate if they have different spatial distribution than the desired light emission events. To this end a weighted radius for a cluster is computed, defined as $R=\sqrt{(\sigma_x^2+\sigma_y^2)/\sqrt{2}}$, where $\sigma_x$ and $\sigma_y$ are the standard deviations of the $q_i$ weighted projections onto the x and y axes corresponding to the column and row axes of the CCD array, of pixels belonging to the cluster. Large events can be eliminated substantially by requiring the radius, R, to lie outside same range of sizes, (referred to the camera input) such that cluster candidates are only confirmed as light emissions if for example R is within a particular range, found by experiment.

4. Assuming that the upper threshold T1 and lower threshold T2 used to identify clusters, are pixel dependent (from a look-up table) further refinements of the criteria used to recognise or define light emissions involve routinely monitoring the camera status (inducing dark level, temperature and gain) to compensate for any drift in operating conditions and adjusting or regularly updating the values of thresholds applied, to take account of any such drift. Refinements such as these give more accurate and efficient detection of light events and improve discrimination between clusters which are caused by light emissions, and clusters caused by other events, which can be thought of as "background".

5. If a first generation image intensifier is used, it has been found desirable to reduce the image intensifier operating voltage to optimise the use of the thresholds described above for light events. Such intensifiers can perform stably over a large range of operating voltages. Both the number of ion envies occurring and the size of S, associated with any ion events which do occur, fall away very rapidly as the operating voltage is reduced. However the number olight emission event clusters and the cluster radius arising from light emissions, remain relatively uncharged so that the size of S, for light emission clusters, falls less rapidly in response to operating voltage drop than does the corresponding sum (S) for ion initiated events.

6. Cluster candidates may be analyzed to see if any arise from two or more overlapping clusters and if so, the separable clusters are stored and independently classified.

7. Parameters to be measured, and values to checked to enable identification and classification, may be determined by subjecting the CCD camera, or intensifier and camera combination to known events and determining the values of different parameters of the signals making up the clusters resulting in the CCD output.

Multi Labelling

In a further refinement, samples labelled with different light emitting material (multi-labelling or dual labelling) can be measured using different filters to select particular ranges of wavelengths for each label. Separate images and lists of the events can be produced pertaining to each separate label material, or the differently identified light emission event labelled accordingly in any listing produced, and displayed in different colours in a single display.

Display of sample image

To assist in analysis the light emission labelling, the invention not only provides the step of displaying on a visual display device the light emission instigated event positions for which coordinates are stored, but also the step of causing to be displayed in correct register with these points an optical image of the sample from which the light has been detected, to enable the regions in the sample for which light is arising readily to be seen.

The optical image of the sample may be displayed as an outline or as a background, and the picture content in the display corresponding to the coordinate defined positions preferably takes precedence over the picture content of the image of the sample.

Features of apparatus embodying the invention

Apparatus for performing the method first described conveniently comprises:

(1) means for addressing separately addressable sub-regions of a cooled CCD or image intensified CCD camera array, (2) charge reading means adapted to investigate the charge in each sub-region during each interrogation of the CCD array and produce and electrical signal indicative of the photon emission activity to which each sub-region has been exposed during the preceding exposure period.

(3) signal processing means adapted to identify clusters of electrical signals indicating that light has influenced the charge on a plurality of immediately adjacent sub-regions during the preceding exposure period, (4) further circuit means adapted to determine the coordinates at the center of each identified cluster of adjacent sub-regions, (5) memory means for storing signals relating to the centre of each cluster of sub-regions, and (6) memory addressing means to read out from said memory means the coordinates of the centres of the identified cluster.

Apparatus as aforesaid may also include a scanning display system to which signals from the memory addressing means can be supplied in synchronism with the scanning so as to produce in the display visually distinctive points at positions defined by the stored coordinate values so as to produce points in the display corresponding to the positions on which light has impinged in the cooled CCD array of a camera during the preceding exposure period. By updating the display on a regular basis, with information from subsequent memory addressing, a picture can be generated in the display indicatiing light omissions as they occur together with those which have already occurred.

The invention also lies in apparatus for detecting the presence and position of light emitting material in a sample, comprising:

(1) CCD camera means, (2) sample support means for the labelled sample, (3) means for repetitively scanning the array of the CCD camera, each scan corresponding to an interrogation of the array and being followed by a resetting step and preceded by an exposure step, (4) means for generating from the scanning a data signal corresponding to the charge pattern found during each said interrogation of the CCD array, (5) signal processing means and computing means to which the said data signals are supplied after each interrogation, and adapted to perform measurements, thereon to identify any cluster of immediately adjacent data values each of which is indicative that light emmited by the sample or image intensifier has been incident on immediately adjacent separately addressable regions of the CCD during the exposure period immediately preceding the interrogation, (6) means for computing from the data signals of each identified cluster the x, y coordinates of a center of the cluster, with reference to the scanned CCD array, and (7) memory means for storing at least the centre coordinates of each identified cluster.

The memory means may advantageously be such as to allow the center coordinates of all clusters identified during the same interrogation of the CCD array, to be stored therein.

Apparatus according to the invention further comprises means for reading out the data in the memory and producing a list of the center coordinates stored therein.

Apparatus according to the invention also comprises a visual display system responsive to signals read out from the memory means thereby to reproduce in the visual display a reproduction of the scanned area of the CCD array, the signals read out from the memory means serving to modulate the visual display so as to generate visually distinctive features in the display at positions defined by the coordinates stored in the center memory.

In order to further reduce noise the CCD may be operated in so-called inverted mode, thereby to further reduce contributions in its output signal due to fluctuations in thermal noise in the CCD array.

Alternatively a non-inverted mode cooled CCD array may be used when fitted with special low noise readout circuits. This in fact enables operation of higher read out rates which further reduce noise integration periods.

In either arrangement the use of multiple stage image intensification ahead of the CCD array enable smaller signals, such as those arising from signal photoelectron emissions, to be handled.

The invention also lies in apparatus as aforesaid further comprising an addressable memory within which information is stored corresponding to the outline and detail of the sample and memory addressing means for reading out from the said memory signals in synchronism with a scanning display device, the signals read out from the memory being supplied to the scanning display device to produce in the display an image of the sample from which the light has been detected by the CCD camera in combination with and superimposed thereon visually distinctive points corresponding in position to the coordinates stored in the first mentioned memory so that the superimposed points are in correct registry with the image of the sample from which the light has been detected to enable the regions of the sample from which light has arisen readily to be seen.

A fiber optic taper may be uses either as or in contact with the faceplate of the imaging system, in which the tapered area corresponds to the area of the photocathode faceplate of the entrance window and the larger area at the input end of the taper corresponds to the area of the sample.

Assays to which the invention may be applied comprise:

1. histological sections of tissue such as animal or plant tissue.

2. high density arrays of oligonuclides, peptides, DNA, proteins, carbohydrates or polysaccharides where the object is the detection of specific target biomolecules in such arrays.

3. viable (growing) cells—adhered onto petri dishes or microscope slides for example cellular monolayers, cell cultures and tissue cultures.

Labelling

This may be achieved in a number of different ways:

1. a drug may be administered to an animal after which a distribution of the drug in the animal is looked for, for example in brain or liver tissue obtained following biopsy or autopsy.

2. a section of tissue or organ is cut to give a thin section of thickness of the order of 10 to 20 microns and the thin section is exposed or incubated with a label or label ligand for example probe or drug for example identification of receptors in cells.

3. in-situ hybridization techniques may be used where labelled nucleic acid probes are hybridized to the tissue section (as in 2 above).

4. the uptake and distribution of labelled material may be measured. For example the uptake of drugs or other biomolecules into cells or organelles within a cell in samples such as tissue sections or cellular monolayers so as to identify the action or cell function for example neurotransmitter in the brain.
5. immunobinding techniques may be used where antibodies labelled for example with a light emitter are used to probe for example antigenic sites in tissue sections or cells.
6. toxicological studies to identify the effect of toxic agents or biomolecules on cell function, for example use of chemical agents on samples of tissue sections or cellular monolayers or cell cultures. An example is the use of cosmetics or compounds in cosmetics on a section of, for example, skin tissue, where the labelled compound or chemical agent is identified to determine the distribution of binding of the compound and the specific areas or cells into which the compound is taken up.
7. dual-labelling techniques may be used where more than one label is to be employed to identify more than one specific target molecule in a given sample. The imaging technique may be used to measure the location of more than one label in the same sample.

Advantages of This System

Light emission from luminescent and fluorescent samples can be very weak requiring a very sensitive photon-imaging detector with wide dynamic range. As described above the system may include, low-noise techniques and high gain image intensification or a cooled CCD camera to capture images of luminescent and fluorescent processes.

This system can quantitatively image the photons emitted by a luminous sample or fluorescently-excited sample of large area (e.g. microtitre plate of 140 mm diagonal), with ultra-sensitivity and high dynamic range. Single photon electron events associated with photon emitting sites in the sample can be localised in the sample with high resolution, namely sub-pixel accuracy (10 micron at the photocathode).

It is also important to note that prior art methods of inspecting photon events using regular fixed size arrays of pixels fall down when large areas of pixels are affected by a photon event, particularly when the pixels do nt confirm to a regular shape and may extent in a number of different directions like fingers from a hand or in a sucke-like manner. The invention overcomes the problem of investigating such pixel arrays by linking pixels into clusters by proximity.

BRIEF DESCRIPTION OF THE DRAWINGS

The invention will now be described by way of example with reference to the accompanying drawings in which:

FIG. 1(b) is a block schematic diagram of another embodiment of the invention.

DESCRIPTION OF THE DRAWINGS

Figure 1A:
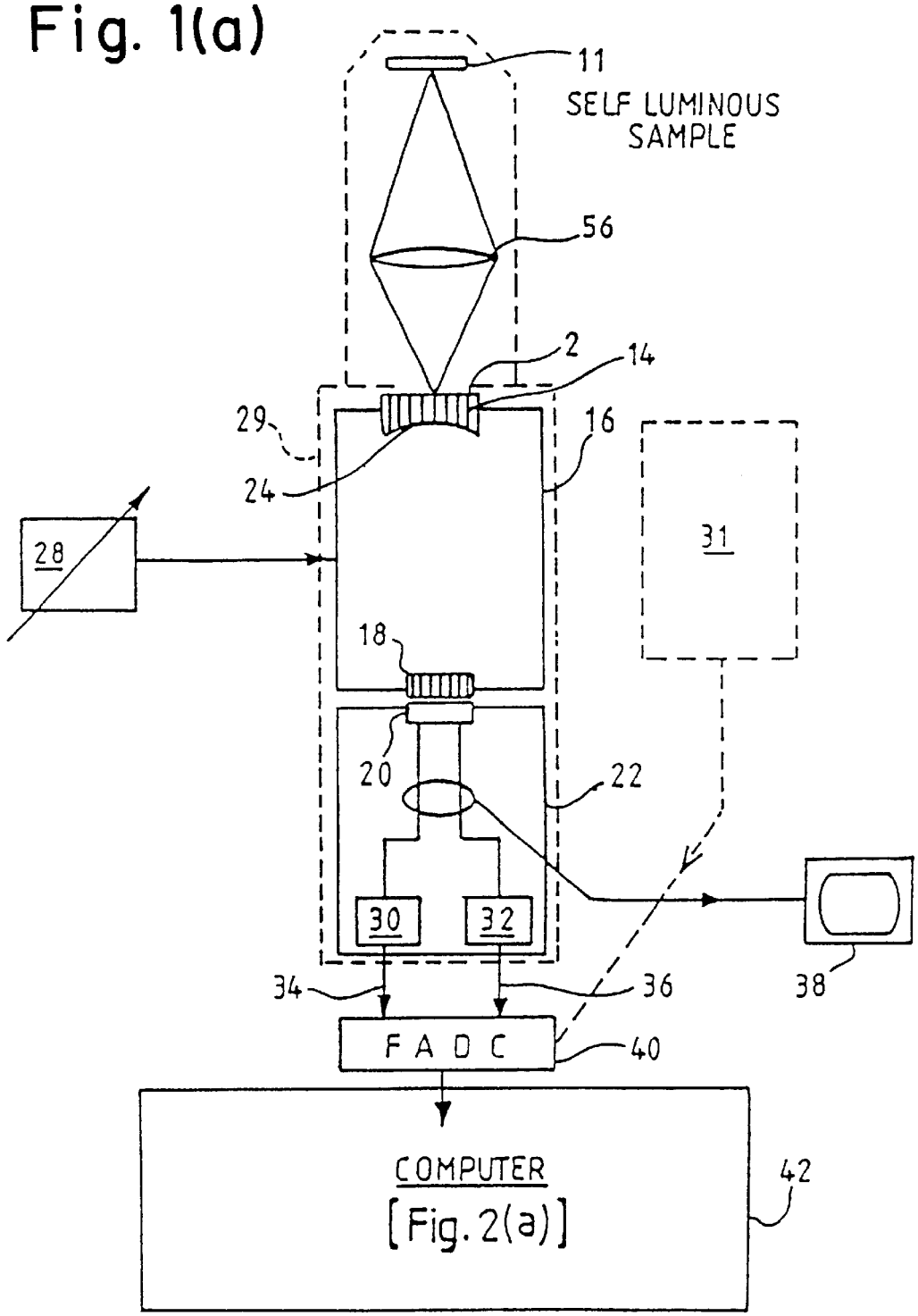
FIG. 1(a) is a block schematic diagram of apparatus embodying the invention for detecting light emissions in a sample.
Figure 1C:
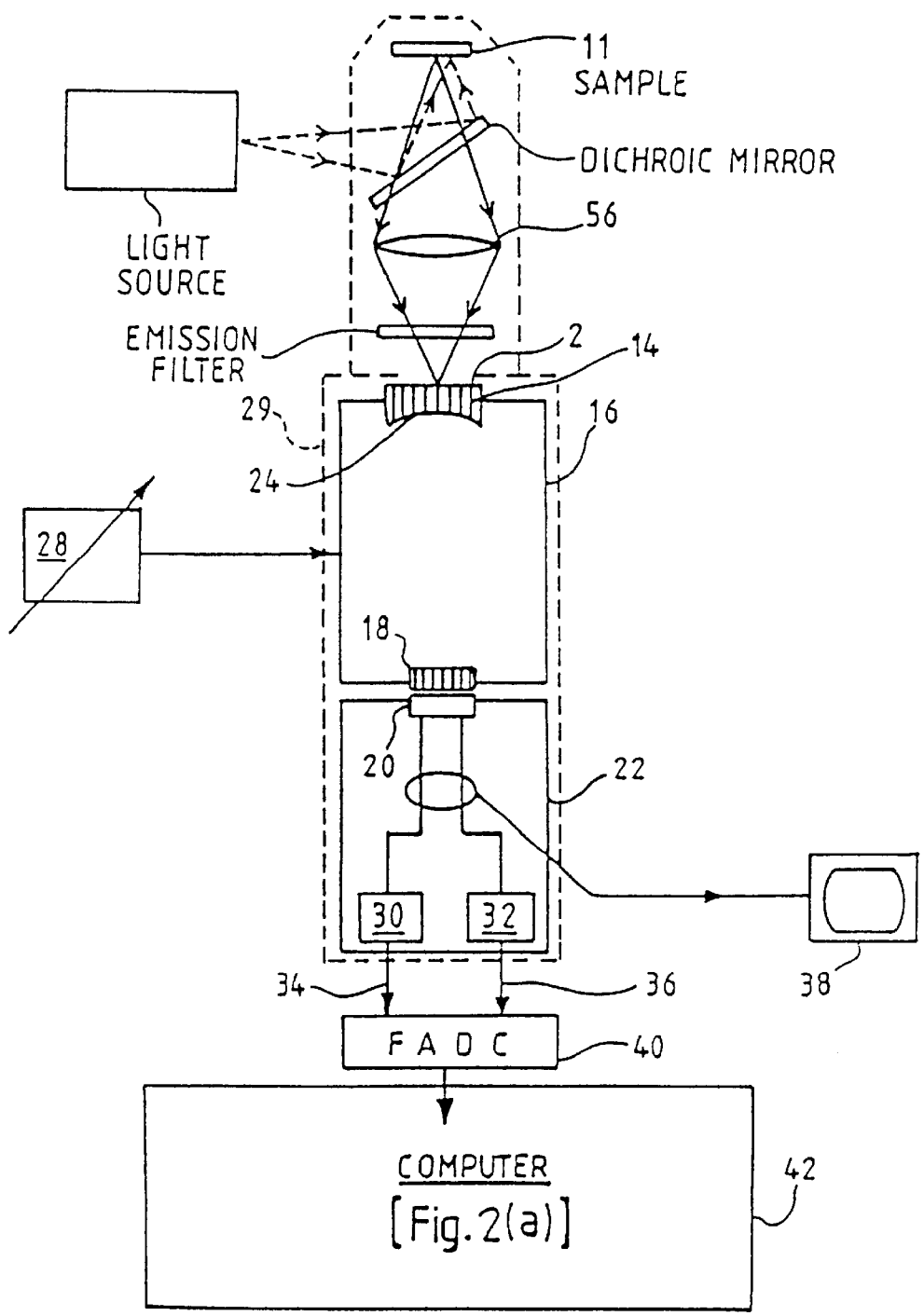
FIG. 1(c) is a block schematic diagram of another embodiment of the invention.

FIGS. 1(a), 1(b) and 1(c) show an imaging system to which light from different sample arrangements is supplied.

FIG. 1(a) shows how a sample labelled with self-luminous material can be imaged using a lens 56 onto the input faceplate of the image intensifier of the camera system 16/22.

FIG. 1(b) shows how a sample can be excited with the light of a chosen excitation wavelength from behind (trans-illumination) and the light emitted by the fluorescing sample is passed through an emission filter to pass the band of wavelengths emitted by the sample and block the exciting light.

FIG. 1(c) is similar except that the sample is excited by light having a selected wavelength received on the near side of the sample to the imaging system (epi-illumination). This requires use of a dichroic mirror to reflect excitation light and transmit emission light, and an emission filter to pass wavelengths emitted by fluorescing sample and to block light of other wavelengths, as shown.

Using fluoresein as the labelling material, an excitation wavelength of 485 mm can be used and the emitted light would typically be in the range 530–650 mm.

Luminescence and Fluorescence Assays

An example of such an assay is DNA material located in discrete regions of the membrane which may be exposed to a second material which is either luminescently or fluorescently labelled. Uptake or binding of this second material to the sample may be caused to take place during an incubation period. Any unbound material can be removed after this incubation period by washing of the sample membrane. The remaining luminescent or fluorescent labelled second material bound to the sample may then be measured.

The luminescent label can be a luminescent molecule which emits photons of a given wavelength or an enzyme (e.g. firefly luciferase or alkaline phosphatase) which can cause a luminescent process to be catalysed resulting in the emission of photons.

The fluorescently labelled second material can be caused to emit photons by excitation with light of another wavelength using the apparatus described above. The fluorescent label may for example be a fluorescent molecule (e.g.

fluorescein) or an enzyme (e.g. alkaline phosphatase) which in turn can cause a fluorescent material to change from being non-fluorescent to fluorescent.

Alternatively many different fluorescent materials can be used as labels in the same assay, by incubating the sample in turn with a number of second materials labelled with different fluorescent materials. Such a technique of multi-labelling is known as dual or multi-wavelength fluorescence. The different fluorescent materials are chosen to have different spectral characteristics of photon emission so that the excitation wavelengths and emission wavelengths may be varied in turn to acquire a measure of the photon emission from the different multi-labels in the sample.

In a further case the sample (e.g. cells or tissue material) may already contain unknown quantities of enzymes (e.g. alkaline phosphatase or peroxidase) which may be required to be measured. Such enzymes could be measured in the luminescence assay by exposing the sample to for example a solution containing luminescent molecules and hence the enzyme would catalyse the emission of photons of light which could be measured in the apparatus. In the example of fluorescent assays, the enzyme would catalyse the production of fluorescent molecules from non-fluorescent molecules which could then be detected as described above.

In FIGS. 1(a) to 1(c) the image intensified representation of the light incident on the window 14 appears at output windows 18 and is transferred to a CCD array 20 of a CCD camera generally designated 22.

The photocathode of the image intensifier shown at 24 is preferably formed from low noise material and is preferably a bi-alkaline material.

A housing forms a hood over the end of the image intensifier input so as to restrict the entry of light or other radiation which otherwise could affect the operation of the image intensifier.

If the sample 11 is of sufficient contrast or is stained, and the support (not shown) is itself transparent or at least translucent, then a light source can be located above the support to obtain an image of the sample using the intensifier CCD camera.

Typically the image intensifier 16 and CCD camera 22 are formed as a unitary assembly and comprise "an image-intensified camera" and to this end the two items are shown joined by the dashed line 29.

Where the sample can only be visually distinguished by the camera using reflected light using for example polarised light, it may be necessary to provide a second CCD camera 31 which is movable into position in place of the image intensified camera 16/22 so as to image the sample and provide an output signal for storage and display, as will be described later in relation to FIG. 2(b). In this event it is anticipated the cameras 31 and 16/22 would be mounted so as to be readily substituted one for the other to allow an image of the sample to be obtained using camera 31 and sample activity detected by the image intensifier camera 16/22.

The CCD array 20 is controlled in known manner by addressing electronics 30, and the signal read out by the addressing of the array during each interrogation cycle of the CCD camera is amplified by amplifier 32. Outputs from the camera are provided along lines 34 and 36, the video output signals being supplied along line 34 and synchronizing (clock) signals along line 36.

An oscilloscope or other visual display device 38 is provided to enable the video output signal from the CCD camera to be displayed before any processing occurs, and to assist in setting up and checking the operation of the equipment.

Figure 2A:
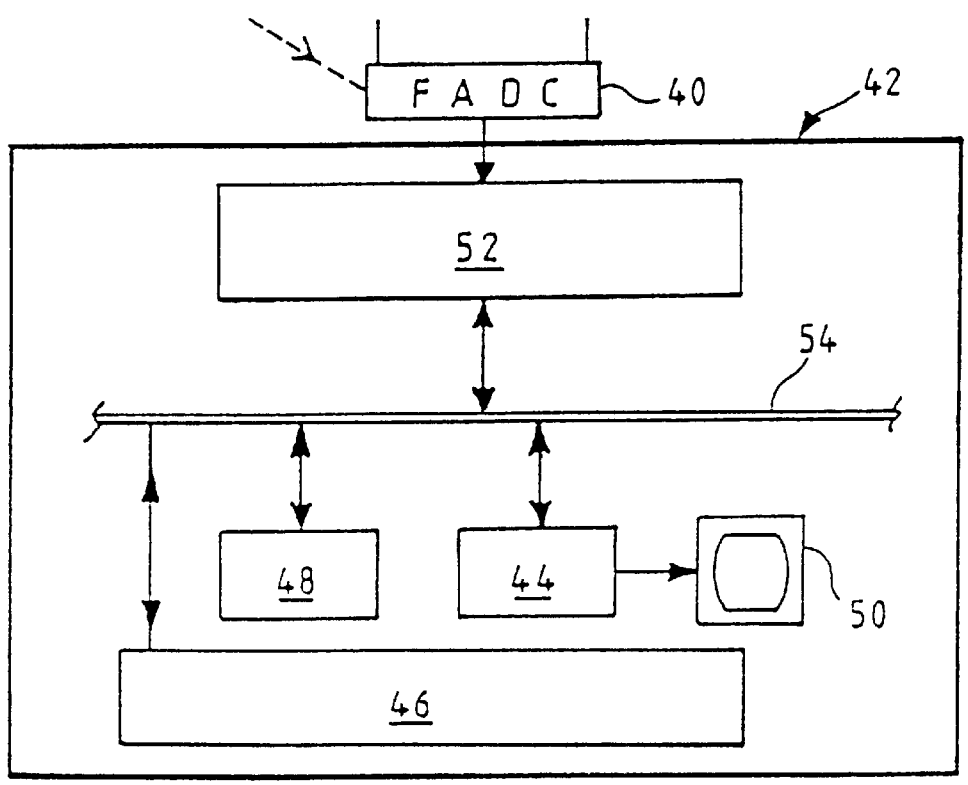
FIG. 2(a) is a block circuit diagram of the contents of Box 42 in FIGS. 1(a) to 1(f)

The signal along line 34 is assumed to be an analogue signal and to this end a fast analogue to digital converter (FADC) 40 is provided so as to provide a digitized video signal for supply to a computer 42 (see FIG. 2(a)), which may for example comprise a standard personal computer (PC) containing a host processor 44, a host memory 46, a large capacity hard disc drive 48 and associated visual display unit or monitor 50. The processing power of the PC can be augmented by using a preprocessor/video compression board generally designated 52 so that a processed signal is supplied to the PC bus 54 instead of the signal from FADC 40.

The provision of additional processing power ahead of the bus 54 is of considerable importance if the speed of data transfer via the bus 54 is inadequate to allow real time processing at high frame rates of the CCD, i.e. if the interrogation of the CCD occurs at intervals of time which are insufficiently spaced apart to allow transfer of the data from each read-out of the CCD to the PC before the next frame of data begins to arrive. In that event one function of the processors 52 is to compress or compact the data before it is applied to the computer bus 54.

Figure 1D:
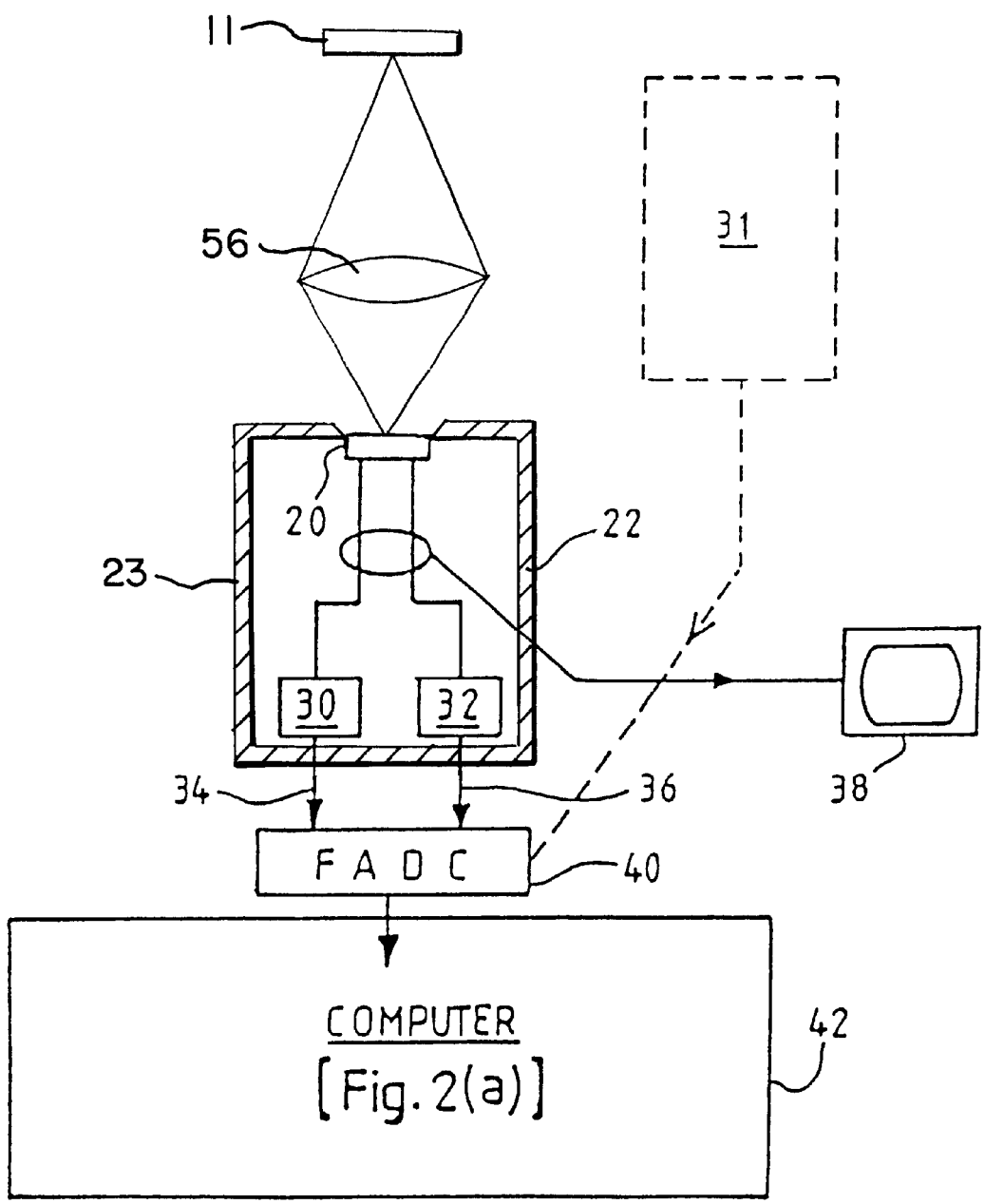
FIGS. 1(d) to (f) are views of arrangements similar to FIGS. 1(a) to (b) respectively, but utilising a cooled CCD camera in place of an image intensified CCD camera.
Figure 1E:
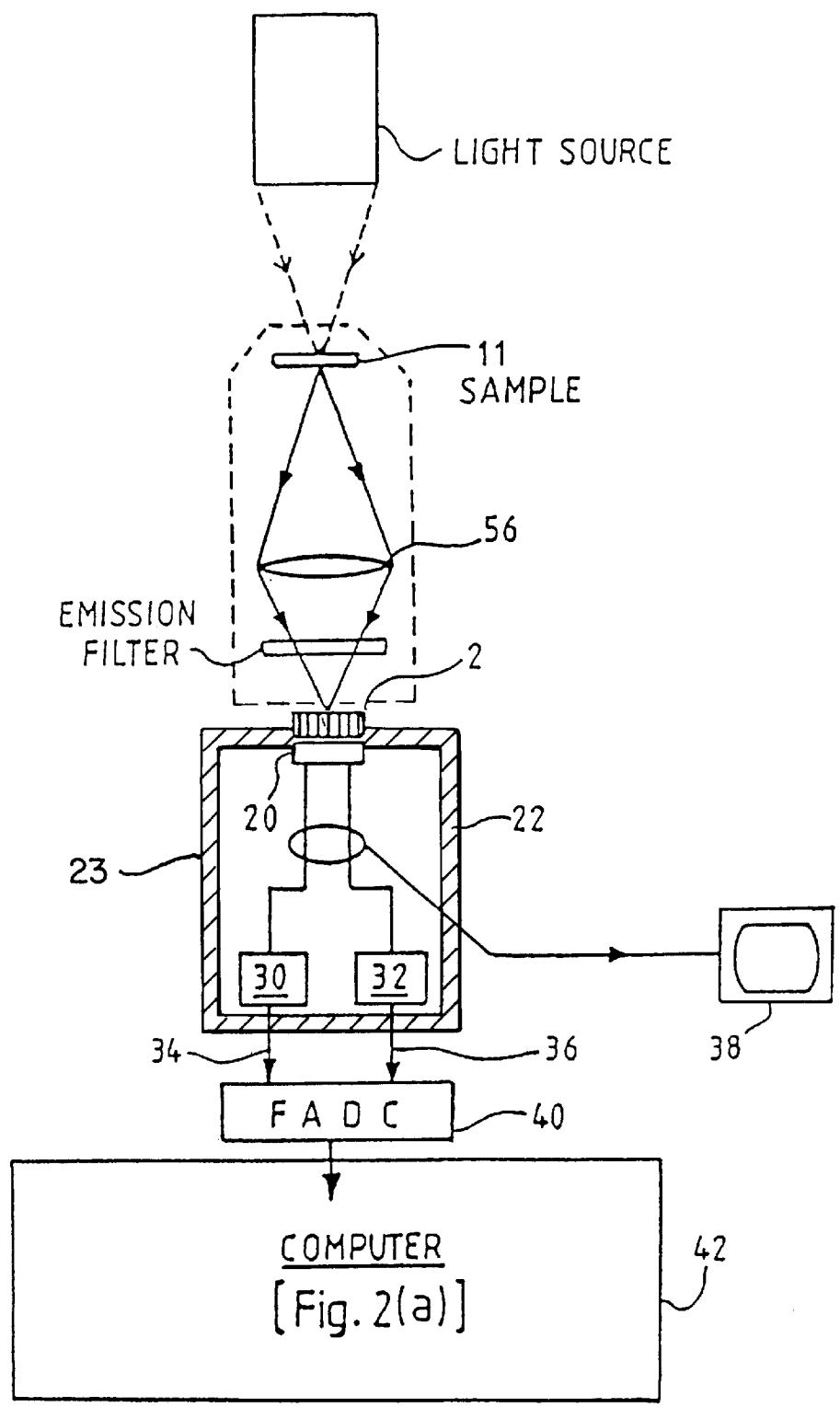
Figure 1F:
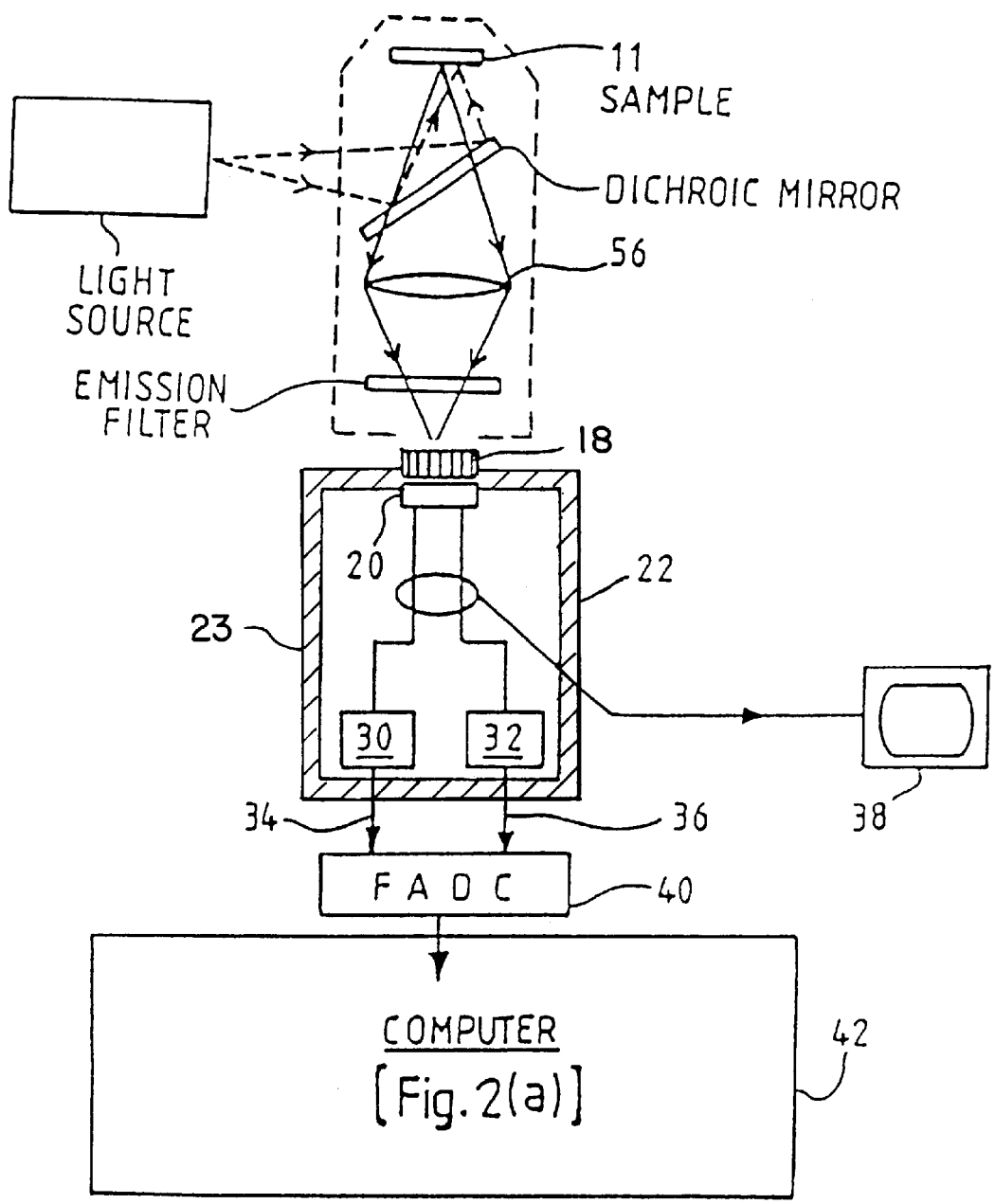

Referring to FIGS. 1(d) to (f) there is shown a modified apparatus which is generally similar to FIGS. 1(a) to (c) respectively. However, in each case here the image intensifier 16 is omitted, and instead the camera 22 is surrounded by a cooling chamber 23. Thus light from the sample 11 passes through the lens 56 and enters directly onto the array 20 of the cooled CCD camera 22. The cooling chamber 23 lowers the temperature of the CCD camera to a sufficiently low temperature as to reduce unwanted electrical noise emissions to a low enough level as to permit low light level events to be identified in the charge pattern of the CCD array after exposure. The cooling may be efected by using a liquid gas in manner known per se.

It is therefore to be understood that reference hereinafter to a CCD camera, unless otherwise stated, are intended to refer either to an image intensified CCD, camera or to a cooled CCD camera.

Detail of Data Processing Computer

Figure 2B:
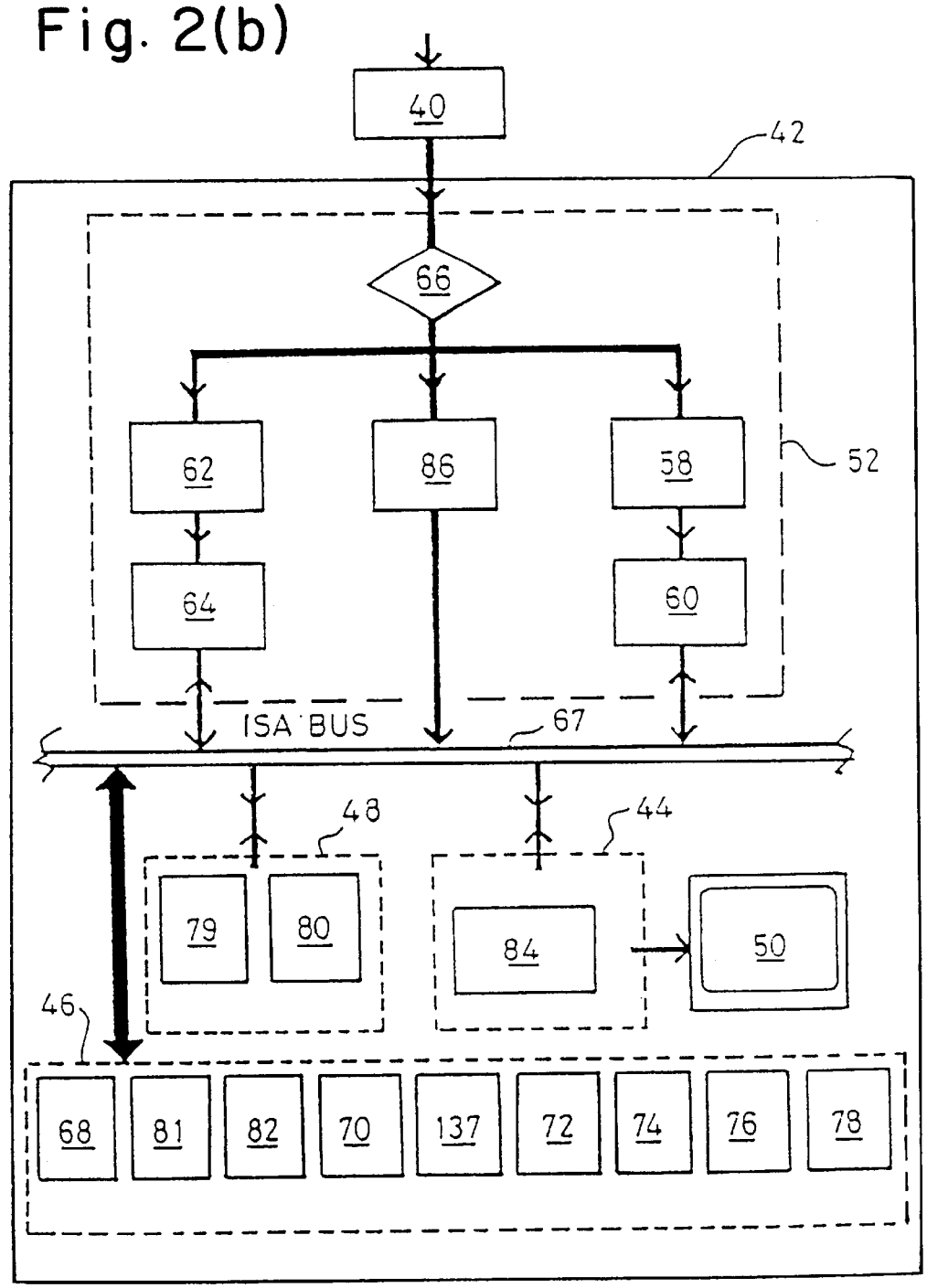
FIG. 2(b) is a more detailed block circuit diagram of the simplified system shown in FIG. 2(a), FIG. 3(a) indicates the logic decision making hierarchy and algorithms of the processing system of FIG. 2.

FIGS. 2(a) and 2(b) are block schematic diagrams of the computing and data processing unit 42 of FIGS. 1(a) to 1(f) typically based on an IBM compatible personal computer containing a type 486 processor 44 and 8 megabytes of RAM 46. The host had disk 48 should be of the order of 320 megabytes capacity. The visual display unit is preferably an SVGA display.

The host memory 46 is divided into different sections for storing data produced by the camera, and the subsequent processing thereof, but the hard disk 48 is organized as the final storage device for the list of detected event coordinates, and as a long term store of the data used to reconstruct the image of the sample in the SVGA display 50 obtained from a preliminary imaging step as already described or from an alternative camera such as 31.

One of the expansion slots of the computer is fitted with a special purpose video processing board 52 previously identified as containing the dedicated processors for compactifying or compressing the data from the FADC 40 and thresholding to achieve noise reduction.

Although shown as mounted separate therefrom, the analogue to digital convertor 40 may be incorporated on the board 52. A suitable device to serve as the FADC 40 is the twelve bit analogue to digital convertor produced by Analogue Devices under the code AD 1671KQ.

On the card there are mounted two processing paths in order to achieve higher operating speed than if only one is used. To this end one path comprises processor 58 and associated frame buffer 60 and the other a processor 62 and associated frame buffer 64. Additional similar parts may be employed if even higher operating speeds are required.

The increase in operating speed is achieved by providing a switch 66 which operates in synchronism with the interrogation of the CCD and diverts the digitized video signal arising from successive interrogations of the CCD array alternately to the processors 58, 62. Processors 58 and 62 perform identical functions on incoming data and each is typically a Texas Instruments type DSP TMS 320C50.

The function of each processor is to compact or compress the data supplied to it via the switch 66. The latter typically comprises a gate array type XILINX XC3030.

Noise reduction and a first level of compression of the incoming data is achieved by each processor 58, 62 by rejecting data values (and their corresponding addresses) which are less than a threshold T3. The data values (and corresponding addresses) which do pass the T3 threshold test are stored in the frame buffer 60 or 64 respectively and typically each comprises a fast static random access memory (SRAM) such as that supplied by Micron under type No. MT5C1008.

During alternate CCD frame periods, (i.e. exposure followed by interrogation) data is supplied by the FADC 40 and switch 66 to the DSP 58 which applies the programmed algorithm to the data in real time so that the processed signal is available for immediate transfer to the associated frame buffer 60 during the frame period, so that at the end of the frame period, DSP 58 is in a position to transfer the processed data in the frame buffer 60 via the ISA computer bus 67 to a frame store 68 in the host memory 46.

Typically the data transfer is effected by direct memory addressing (DMA) across the ISA bus 67.

Since the time for this data to be transferred is not inconsiderable and the processor cannot handle signals from the next frame until it has transferred all the data into the frame store 68, the data from the other set of alternate frames is directed to the other processor 62 by appropriate operation of switch 66. Operation of DSP 62 and the frame buffer 64 is similar to that of 58 and 60 and it will be seen that the whole of each frame period is available to one or other of the processors to either process incoming data or transfer processed data into the frame store 68. Each transfer replaces the data previously stored by the other processor. Thus whilst one processor such as 58 is transferring data from its frame buffer, switch 66 diverts incoming digitised data from FADC 40 to the other processor and during the next frame period, the process is reversed by operation of switch 66 so that the incoming data is now supplied to the other processor whilst the first processor transfers the processed data in its relevant frame buffer to the frame store 68.

Provided the number of separate addresses and data values greater than T3 is less than 50% of all the possible addresses making up each frame, the T3 thresholding algorithm will reduce the volume of data per frame. The frame rate is then dictated by the time needed to transfer this reduced volume of data from the relevant frame buffers 60 and 64 into the frame store 68.

The compression/compactification function performed by the DSP's 58 and 62 is necessary if (as is usual) the data transfer rate of the host processor I/O bus 66 is insufficient to permit video signal data from FADC 40 to be transferred fast enough to permit useful frame repetition rates of the CCD to be achieved. If the host processor I/O bus data transfer rate is high enough, then the special input card allowing data compactification may not be required.

Further data compression can be obtained by omitting from the data to be transferred the second and subsequent addresses of immediately consecutive pixels which satisfy the threshold T3, following standard compression algorithms.

The scheme described requires a means of identifying each data item as either an address or data value. An otherwise unused bit in each data item can be used for this purpose.

Where the data is in a sequence of address, data, address, data, etc., etc., standard compression algorithm techniques can be employed to permit further compression of data.

The host processor 44 is programmed to operate in a plurality of different modes, one of which is to identify clusters of data values which are greater than T3 (and their corresponding addresses), and the precise data processing route followed by the processor to achieve that identification is described in more detail with reference to FIGS. 3(*a*) and 3(*b*). The cluster finding operation requires a number of working data stores to be associated with the host processor. The host RAM is therefore organised to provide not only the frame store 68, into which the incoming data values and addresses are stored, but also a cluster pixel store 70, a cluster store 72 in which the computed coordinates of the cluster centres are stored, a threshold store 74, a frame cluster store 76 and a multi-cluster pixel store 78, the function of each of which will be described as the algorithms are described in more detail later. Suffice to say, the coordinates which end up in the cluster store 72 at the end of each frame are transferred to a cumulative cluster store 80 on the hard disc 48. The coordinates may be stored in database format or simply as a list in the cumulative cluster store 80.

The processor 44 is arranged to drive the SVGA display 50 so as to produce thereon an image of all the events for which coordinates are stored in the cumulative cluster store 80 in registry with an image of the sample as seen by the camera. To this end the host processor 44 is adapted to transfer the data which has previously been stored on the hard disc in frame store 79 and which relates to at least the sample outline, to a screen store 81 which forms part of the RAM 46 and to transfer the coordinates stored in the cumulative cluster store 80 on the hard disc to a second screen store 82 comprising yet another part of the RAM 46. Synchronous high speed repetitive addressing of stores 81 and 82 enables a video signal to be formed for controlling the SVGA display 50 and providing therein the desired display of the events superimposed on the outline of the sample.

It is to be understood that the data relating to the sample outline need not be derived from only one interrogation of the CCD array but advantageously may be derived from a succession of such interrogations whilst the sample is suitably illuminated as by the light source 26. Since little or no processing of the data arising during these interrogations is required, a direct link from the switch 66 to the ISA bus 67, via a buffer amplifier 86, may be provided on the video input board 52. The processor 44 is programmed to instigate the direct link during the appropriate interrogations of the CCD array and to direct the data via the ISA bus to the hard disc from where it can be read into the screen store 81 when required.

When a sample is replaced with the next sample, the sample image data on the hard disc has to be overwritten by a subsequent imaging of the new sample via the CCD camera. The first sample can be saved elsewhere on the hard disk as required.

The events determined by the coordinates in the cluster store 72 and repetitively read out from store 82 are displayed in a contrasting colour or manner in the display 50. By updating the store 82 on a regular basis, an indication of all the emitter light sources which occur since the beginning of an evaluation of a sample can be displayed in real time.

The programming of the host processor 44 to perform the cluster finding function (designated 84 in FIG. 2(*b*)) can best be understood by studying the logic flow chart of FIG. 3(*a*).

This function is to find and analyze clusters of data values which satisfy certain threshold criteria and for the purpose of this analysis it is helpful to consider the relationship between the CCD array and the digital data values descriptive of the charge pattern on the array after exposure to light.

If the charge from each separately addressable light sensitive region in the array is digitized, and each such region is mapped on a one to one basis with corresponding regions in a display device, and the light produced by each region in the latter is controlled by the digital value associated with the corresponding region in the CCD array, then the smallest resolvable point in the display (normally referred to as a pixel) corresponds to the separately addressable regions mapped into it from the CCD array. Each separately addressable region of the CCD camera can therefore be thought of as a pixel.

The same reasoning applies whether or not the CCD array is addressed in a manner so as to produce a sequence of digital values or produces an analogue value which is then digitized by means of an A to D convertor operating synchronously so as to digitise the analogue signal values as if each was arising from an addressing of the corresponding point in the display.

The value of q (the digitized value of the charge at each pixel) is obtained by the analogue to digital converter 40. This operates so as to convert the charge related voltage signal obtained during interrogation of the CCD array into a series of digital values one for each pixel and if a 12 bit analogue to digital converter is used, the saturation charge in each pixel will be given a value of 4095 and intermediate values of q less than saturation, a value in the range 0 to 4095.

The process for cluster finding begins at box 102 on receipt of a frame ready signal. Control first passes to box 104 and then to 106 where the row address r and the column address c are each set to 1 so as to address the first pixel of the frame.

Stepwise Investigation of the Pixels in the Frame

The boxes marked 104, 106, 108, 110, 112 and 114 show how r and c are incremented to allow each pixel in turn in the frame to be examined. As each pixel is processed, control arrives at box 114, where the column address c is incremented by 1. The value of c is tested in box 110 and if c is less than or equal to the maximum value allowed (namely value C), processing continues in box 112. If c exceeds C, control passes to box 108 where the row address r, is incremented by 1 and the column address is reset to 1 (box 106).

Control now returns to box 110 and from there to box 112 where the row address r is tested against the maximum row address value R. If r exceeds R, it means that the last of the pixels in the CCD array has been seen and all the pixels in the CCD frame have been tested.

Box 116 temporarily takes over at this point to perform a transfer of data to the accumulation cluster store 80 (to be described). Control then returns to box 102 to await the frame ready signal indicating the beginning of the next frame when the process is repeated.

Thus all valid r and c combinations in turn reach box 118 where, for each identified pixel, the associated digital pixel charge value q is compared with a threshold T1 stored in a threshold store 74.

If q is below T1, control temporarily returns to box 114 so that the next pixel address can be generated and the next pixel q value can be determined.

If the q of the identified pixel exceeds T1, control instead passes to box 120 which causes a new cluster to be started in the cluster pixel store 70.

The r, c and q values for the identified pixel (which becomes the seed pixel of the new cluster) are passed to box 122 which now assumes control.

Using the values of r, c and q in 122, box 124 now attempts to build a cluster around this seed pixel. Starting with this seed pixel, the building algorithm checks for any pixels adjacent the seed pixel which have q values exceeding a second (lower) threshold T2 and which are thus deemed to form part of the new cluster. The algorithm proceeds by continuing to add to the cluster the r and c values of all immediate neighbours of both the seed and any pixels already identified as belonging to the cluster, until no immediate neighbouring pixel is found having a q value that exceeds T2. During this process the action of box 126 is to assemble in the cluster pixel store 70 the r, c and q values of all of the pixels which make up the cluster.

When the end of the cluster is reached, box 128 computes certain parameters for each cluster, including the number of pixels (N), the sum of the counts (S) the centroid of the cluster and the radius (R), of the charge weighted distribution of the pixels in the cluster by using the r, c, q values of all the relevant pixels in the cluster store 70.

A number of pixels (N) is calculated by simply counting the number of different r, c coordinates entered in the cluster pixel store.

The sum of the counts (S) is calculated by adding the q values of the same pixels.

The cluster centroid coordinates ($r^{cent}$, $c^{cent}$) are calculated using the following equations:

$$r^{cent} = \sum_{i=1}^{N} r_i q_i \bigg/ \sum_{i=1}^{N} q_i$$

$$c^{cent} = \sum_{i=1}^{N} c_i q_i \bigg/ \sum_{i=1}^{N} q_i$$

The computed cluster centroid coordinates ($r^{cent}$, $c^{cent}$) are placed in the cluster store 72. The value used in these formulae will normally have been corrected for dark level variation, as by having the appropriate dark level value $b_i$ subtracted first.

In these equations the index i, of pixels to be summed, takes the values 1, 2, 3 etc. up to N, where N is the total number of pixels in the cluster. Thus ($r_i$, $c_i$, $q_i$) refer to the row address, column address and pixel "count" value for the ith pixel in the cluster. It is important to note that whereas r and c are integer values in the range 1 to R and 1 to C respectively, and are defined by the structure of the CCD, (i.e. the number of separately addressable regions in the array), $r^{cent}$ and $c^{cent}$ are floating point values not limited to integer values. Hence the centroid position can be computed to sub-pixel accuracy.

Another cluster parameter to be calculated is the cluster radius R which is a measure of the area and charge area of the cluster and is computed in two stages. Firstly the product of the q value for each pixel and the square of the r and c projections of the distance of each pixel in the cluster from the centroid, is computed, and each is summed for all pixels in the cluster and normalised by dividing the sum by the sum of the counts (S) for the cluster. This gives $\sigma_y^2$ in the case of the r projections, and $\sigma_x^2$ in the case of the c projections. The effective radius R is computed using the following equation: $R=\sqrt{(\sigma_x^2 \sigma_y^2)}/\sqrt{2}$, where the values of $\sigma_x^2$ and $\sigma_y^2$ are calculated using the following equations:

$$\sigma_y^2 = \sum_{i=1}^{N} q_i (r_i - r^{cent})^2 \bigg/ \sum_{i=1}^{N} q_i$$

$$\sigma_x^2 = \sum_{i=1}^{N} q_i (c_i - c^{cent})^2 \bigg/ \sum_{i=1}^{N} q_i$$

The resulting value of R namely the cluster "radius", is placed in the cluster store 72 in association with the other parameter values for the cluster.

Box 130 compares the parameter values in the cluster store 72 with predefined acceptance values for these parameters held in the threshold store 74. A cluster will be rejected if the number of pixels N is too small or too big, or if the calculated radius R is too small or too big. The acceptance values can be selected so as to remove the (r,c) coordinates of events whose R and/or N values identify them as for example arising from an ion event from the image intensifier, but retain the (r,c) coordinates of events caused by photons emitted from the sample.

Box 132 determines the overall result of the comparison tests in 130 and passes control onto box 134 if it is determined that the cluster should be accepted, or to box 136 if the cluster is to be rejected.

Box 134 places the contents of the cluster store into the frame cluster store 76 which serves to record the parameters of all the clusters identified as "emitter event clusters", found during one particular frame.

Box 136 sets to zero the digital pixel count values, q, associated with all the pixels belonging to the "emitter event cluster" just processes, so as to prevent any pixel that has been linked to one cluster being identified as a seed pixel thereby instigating a false cluster during a subsequent analysis of pixel values. By setting the q values to zero, these pixels will now be less than T1 and T2, and will hence fail the T1, T2 test as the frame data is checked in Box 118 or 124.

Control then returns to box 114 to permit the next pixel to be identified and processed.

As already stated, after all the pixels in a frame have been considered, control is passed to box 116. This transfers the contents of the frame cluster store 76 into the cumulative cluster store 80 on the hard disk 48 so as to retain the parameter values of all "emitter event clusters" from all of the frames.

It is to be noted that the threshold values T1 and T2 used in the procedure are determined by prior calibration and may be constant or dependent on the values of r and c.

Constant values of T1 and T2 mean the dark level variation (as between one region and another) of the CCD array, is not taken into account and this can result in errors in the selection of pixels belonging to a cluster.

To compensate for this, T1 and T2 are varied depending on the position of the pixel under consideration at any instant, and to this end a look-up table of dark level "correction" values for each of the pixel positions in the CCD array is stored in a further store 137 which conveniently forms part of the host memory 46.

The look-up table data may be stored in a permanent form on the hard disk 48 having been derived from an appropriate interrogation of the CCD array during a calibration interrogation of the CCD array.

The dark level correction data is thus available on the hard disk and can be read into the store 137 of the host memory 46 ready for use whenever the computer is turned on. The data on the hard disk can of course be up dated by appropriate interrogations of the CCD array either at regular intervals, or in the event that a monitored parameter such as the temperature of the CCD array, rises above or falls below preset limits.

The new values obtained by the subsequent dark level interrogation of the CCD array are substituted for those in the store 137. If the change is of a more permanent nature, the values on the hard disk may be rewritten.

In calculating T1 and T2 the dark level correction signals may be employed by adding to the dark level in any pixel different offsets for T1 and T2 so that the value of T1 and T2 varies in accordance with the variations in the dark level across the array. Threshold values are therefore caused to vary from one pixel to another to accommodate variation in the "dark level" of the camera. By this means the criterion for identifying pixels as cluster seeds or cluster members can be made substantially constant across the whole of the camera field of view.

Alternatively, the offsets themselves may be made to vary from pixel to pixel in proportion to any gain variation of the camera across the CCD array. This will then make substantially constant the criterion for identifying pixels as cluster seeds or cluster members across the field of view, to allow for both dark level variations and gain variations.

Alternately the dark level correction signals and the gain variations associated with each pixel may be used to modify the q value in the pixel in subsequent read-out, in which event the thresholds T1 and T2 can remain constant.

Figure 3A:
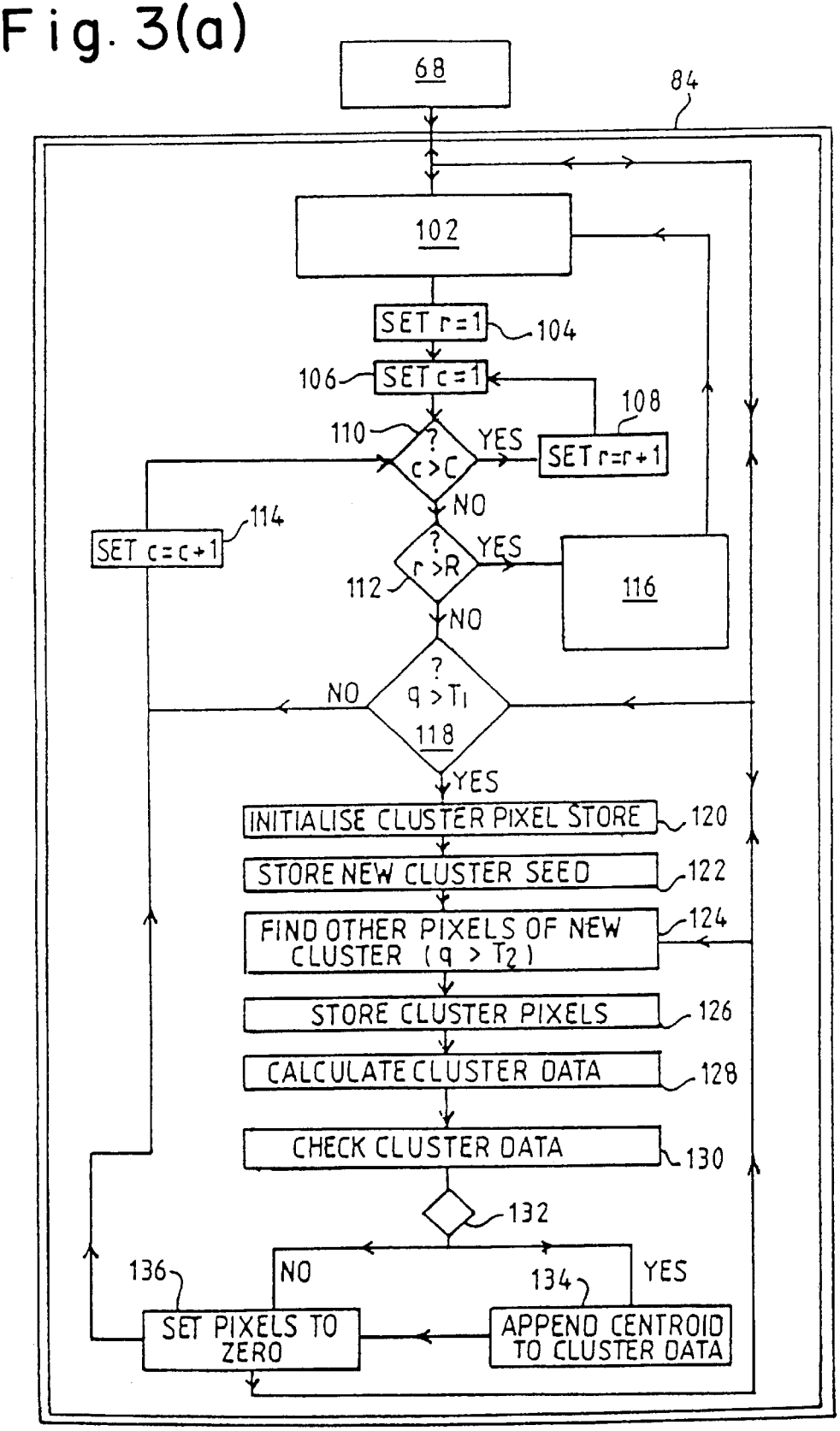
FIG. 3(b) is an elaboration of the processing logic of FIG. 3(a)

FIG. 3b shows a preferred version of the cluster finding process described with reference to FIG. 3a, in which additional features are incorporated to allow for the possibility that some clusters which might be found using the logic of FIG. 3a, may in fact consist of more than one event.

The probability of such overlapping events causing "multi-cluster" formation, increases with sample activity.

The path between boxes 126 and 128 in FIG. 3a, has been extended in FIG. 3b, to include a test for overlapping clusters in box 138.

Box 138 runs an algorithm to check if the cluster values passed from box 126 in fact contained data from more than one event. This condition is defined as occurring if a cluster identified by the FIG. 3a logic is found to contain two or more well separated pixels whose q values are both greater than the threshold T1.

To this end a two dimensional profile of the q values belonging to the cluster pixels in the cluster pixel store is searched to see if it corresponds to a single peak or to two or more peaks, with clear valleys between, (where a "valley" implies a string of connected pixels whose values are significantly below the peak values).

If only one peak is identified for the cluster, no further action is taken since it is accepted as only one cluster.

If however, two or more "peaks" (as defined above) are detected, control passes to box 140 where the pixels making up the cluster pixel store are divided into two (or more) separate clusters, centered on the individual peaks, and are stored in a multi-cluster pixel store 78 in FIG. 2.

The values between the peaks are used to define the boundaries between each separated cluster, and pixels in, or near, valleys may have their values apportioned between two or more such overlapping clusters.

In box 142, a counter is set to the number M of separate clusters, and in box 146, each of the separated clusters is uniquely identified with a number in the series 1 to M. Box 146 passes the "r,c,q" values for the pixels belonging to each of the M separated clusters in turn, to box 128, for its parameters to be computed (as described above) to allow it to be classified as a emitter event cluster or not. After the Mth cluster has been analyzed and classified control returns to box 114.

Choice of Intensified CCD Camera

A preferred camera consists of three components all of EEV design and manufacture, integrated into a complete intensified CCD camera assembly for interfacing to the data processing circuits described with reference to FIG. 2(*a*) and 2(*b*).

In one example the camera comprises:
1. An image intensifier stack consisting of two EEV/ 8370A/25:18 mm demagnifying, first generation, electrostatic focus, image intensifiers using modified cathodes of Bi-alkali type giving low EBI and low red sensitivity, combined with integral high voltage multipliers with intensifier stack earthed at both ends by using extended output to optic stand off up to 30 kV, followed by an non-demagnifying stage such as an EEV/8370A/25:25 device;
2. A CCD image sensor comprising an EEV/CCD 02-06 frame transfer scientific image sensor having the following characteristics:
   a. 512 addressable regions (pixels) per line and 512 lines per field,
   b. each addressable region (pixel) being 22 microns square,
   c. a pixel capacity greater than 300,000 electrons,
   d. non-anti-bloomed for 100% fill factor,
   e. a fiber-optic input window bonded to the image area, and
   f. a modified special low noise, on-chip, output amplifier to minimize readout noise.
3. A CCD driver capable of 18 MHz pixel output rate to drive the CCD 02-06 sensor, and having the following characteristics:
   a. a read-out noise performance of less than 30 electrons RMS per pixel with the CCD operating at 18 MHz pixel range (excluding dark current shot noise),
   b. analogue, low impedance video output and logic level synchronisation pulses, and
   c. an electrically reprogrammable gate array, programmed to drive the CCD sensor and provide signals required to interface correctly and efficiently with the processing system of FIGS. 2(*a*) and 2(*b*).

In another example of the camera the first of the three image intensifying stages may to advantage demagnify in the ratio of 40:18.

Alternatively a 65:25 demagnifying fiber optic taper may provide the input to the first image intensifier of a group of three where the first is a 25:18 demagnifying image intensifier.

The use of larger area input devices provide means for observing larger area samples with greater efficiency than is available otherwise, whether lens imaging or contact (direct) imaging is employed.

Adjustment of Threshold T3

Normally the value of threshold T3 described in relation to FIG. 2, will be set at a value less than or no greater than threshold T2, since otherwise pixels belonging to a cluster may be lost. If T1 and T2 are pixel dependent values to take account of CCD dark level variation (and gain variation), then the value of T3 will also need to be made pixel dependent (and gain dependent) and a look-up table of values for T3 provided (or a table of offset values for adding to T3) and the processor 44 must be programmed to cause the readout of the appropriate value in synchronism with the interrogation of the CCD array, so as to provide appropriate values of T3 for the different addressable regions (pixels) in the array, as the latter is addressed during each interrogation step.

Higher Speed Option

Figure 4:
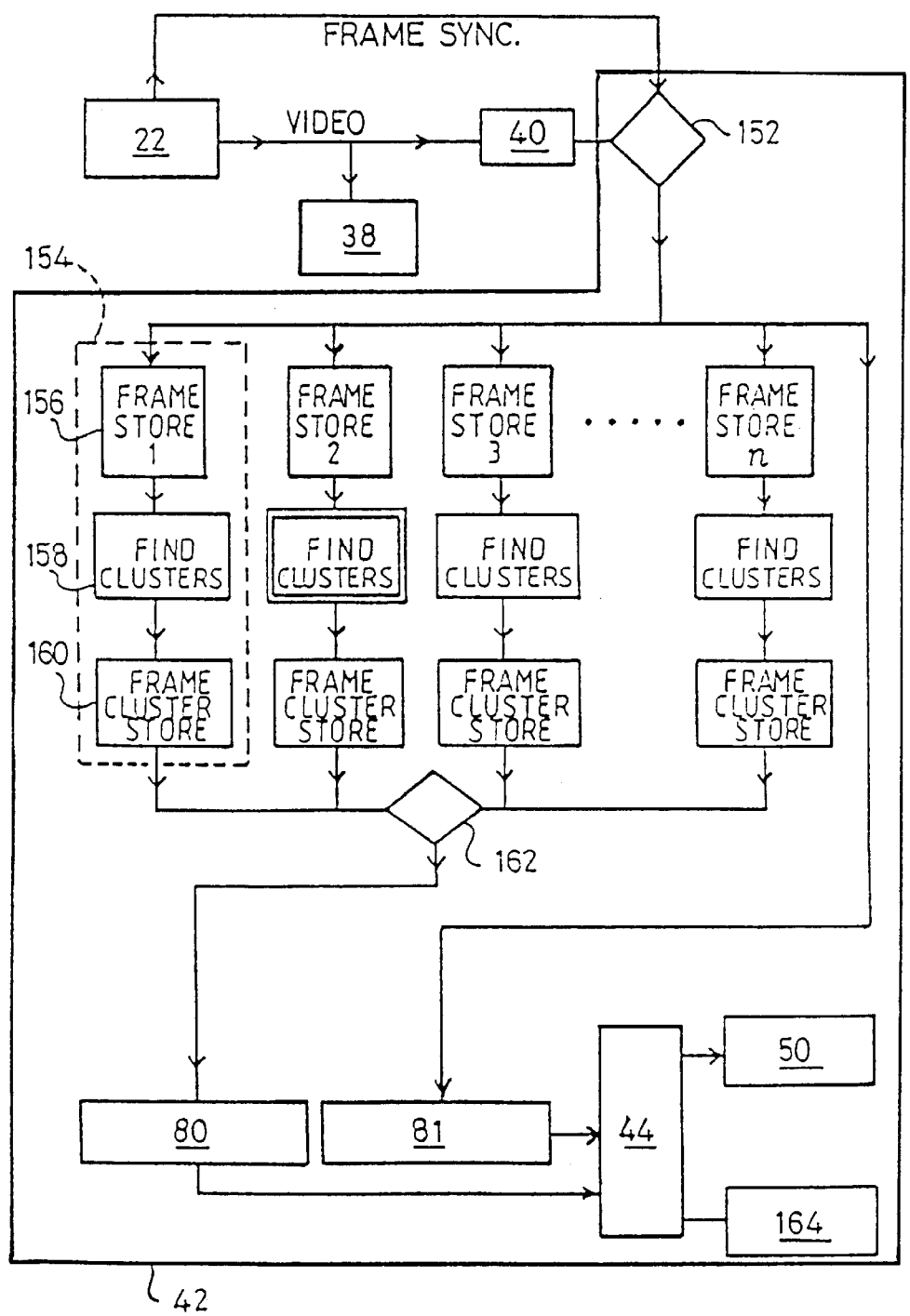
FIG. 4 is a modification of the system shown in FIG. 2 for higher speed data processing.

FIG. 4 shows a variation of the computing and data processing section 42 of FIG. 1*a*.

The different approach enables data to be processed at even higher speed by using a series of parallel processing lines each of which is supplied with data from each one of a succession of frames thereby allowing more time for the cluster finding and cluster identification steps to be performed on the live data.

To this end the output from the camera 22 via FADC 40 is supplied to a multiplexer 152 which serves as a data switch for transferring data first to one and then another in turn of a series of parallel data processing lines, one of which is identified by dotted outline 154. Each line includes a frame store 156, a processor 158 programmed in the same way as the host processor 44 in FIG. 2 is programmed to find clusters, and a frame cluster store 160 for storing the data relating to identified clusters from the frame of data temporarily held in the frame store 156.

By providing n parallel lines, the time available for processing to find clusters and identify wanted clusters from unwanted clusters, can be made equal to n times the frame period of the CCD camera 22.

Each of the n frame cluster stores 160 is synchronously addressed in succession by a second multiplexer 162 which transfers in turn the cluster data from each of the frame cluster stores 160 to the cumulative cluster store 80 on the hard disc of the host computer. The operation is under the overall control of the host processor 44 which in turn allows the data from the screen store 81 and the cumulative cluster store 80 to be displayed in a SVGA display monitor 50 as previously described and also enables the x, y coordinates with or without photon activity related data to be output for numerical analysis for example as a print-out via a printer 164.

To enable the highest possible speed to be obtained, each of the lines 154 is preferably configured independently using an appropriate digital signal processor and a high speed readable and addressable random access memory associated therewith to provide the frame store and frame cluster store associated with each processor each of which is conveniently a Texas Instruments DSP.

Figure 5:
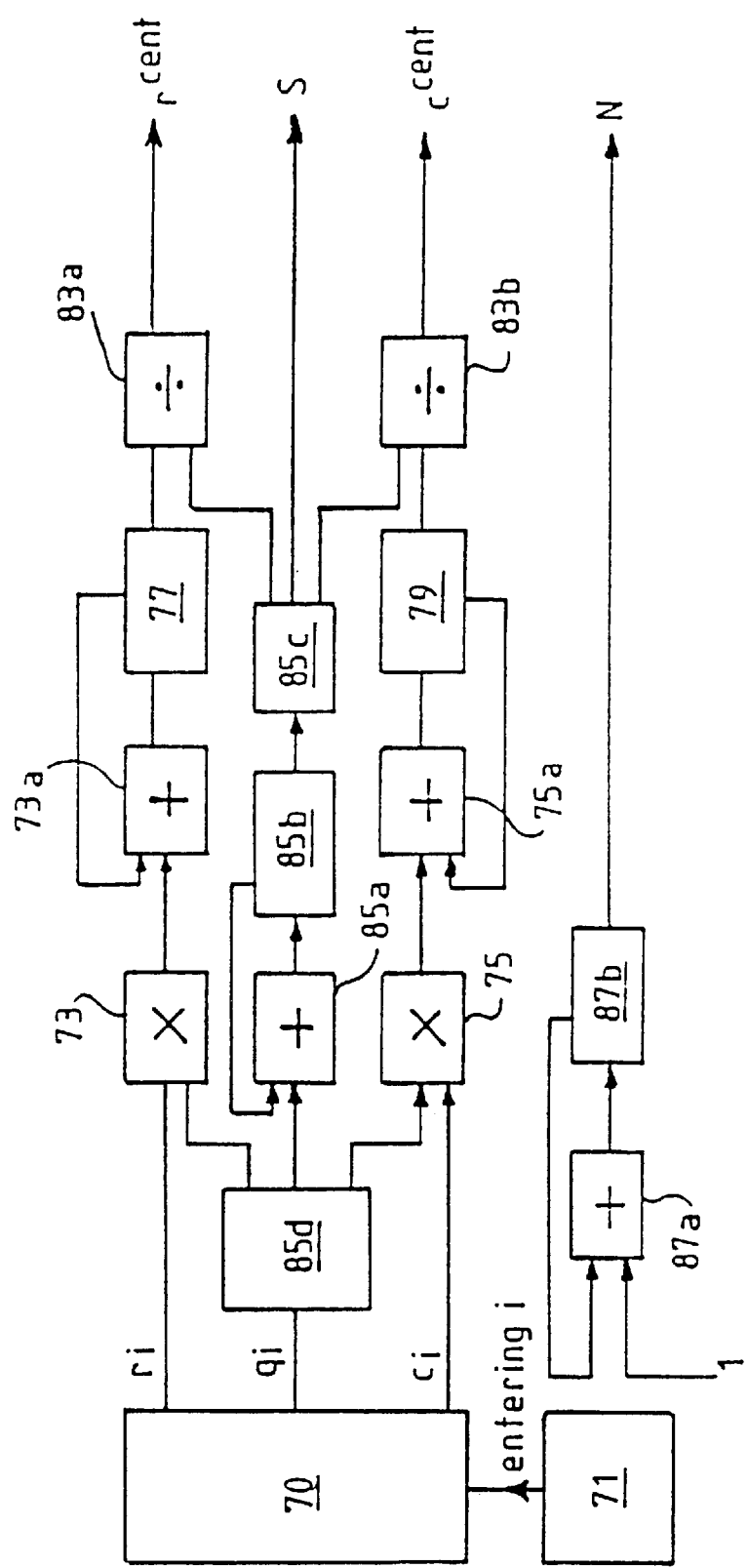
FIG. 5 is a block schematic logic diagram illustrating how the different values $r^{cent}$, $c^{cent}$, S and N are computed for all pixels in the range 1, 2 . . . N.

FIG. 5 shows a logic array for calculating S, $r^{cent}$ and $c^{cent}$ for a group of pixels in a cluster which could be used in place of a single programmed processor such as 44.

The list of ($r_i$, $c_i$, $q_i$) values is stored in the Cluster Pixel Store 70 which is implemented in RAM.

The Index Store box 71 is logic which counts through the pixel values stored in the Cluster Pixel Store 70 and causes each set of ($r_i$, $c_i$, $q_i$) values to appear on the outputs of that store 70 in turn.

These values are passed out to Multiply boxes 73,75 where $q_i$ $r_i$ and $q_i$ $c_i$ are calculated.

The sums of the $q_i$ $r_i$ and $q_i$ $c_i$ are accumulated in the two Buffers 77,79 via the Sum boxes 73a,75a and the Feedback from the Buffers. (The buffers are assumed to be initialized to zero at the start of the calculation).

The buffer and feedback implement the code fragments: buffer=buffer+$q_i r_i$ etc for 73a and buffer=(buffer+$q_i c_i$) for 75a.

At the end of the sum the final buffer contents are passed to two Divide boxes 83a and 83b, where division by S is performed.

The central path of sum box 85a, buffer 85b and fan out box 85c, computes the sum of the $q_i$ values in a similar fashion and hence provides the value of S needed for the divisions shown.

The Fan Out boxes such as 85c and 85d are simple devices which produce identical parallel outputs from a single input.

The last path of sum box 87a and buffer 87b, calculates the value of N by summing the value "1", as many times sequentially as there are pixels comprising a cluster in the cluster pixel store.

Details of the initialization and gating to pass the final contents of the summation buffer memories on to the divide boxes are not shown. The final results are passed to memories (or latches) also not shown.

Figure 6:
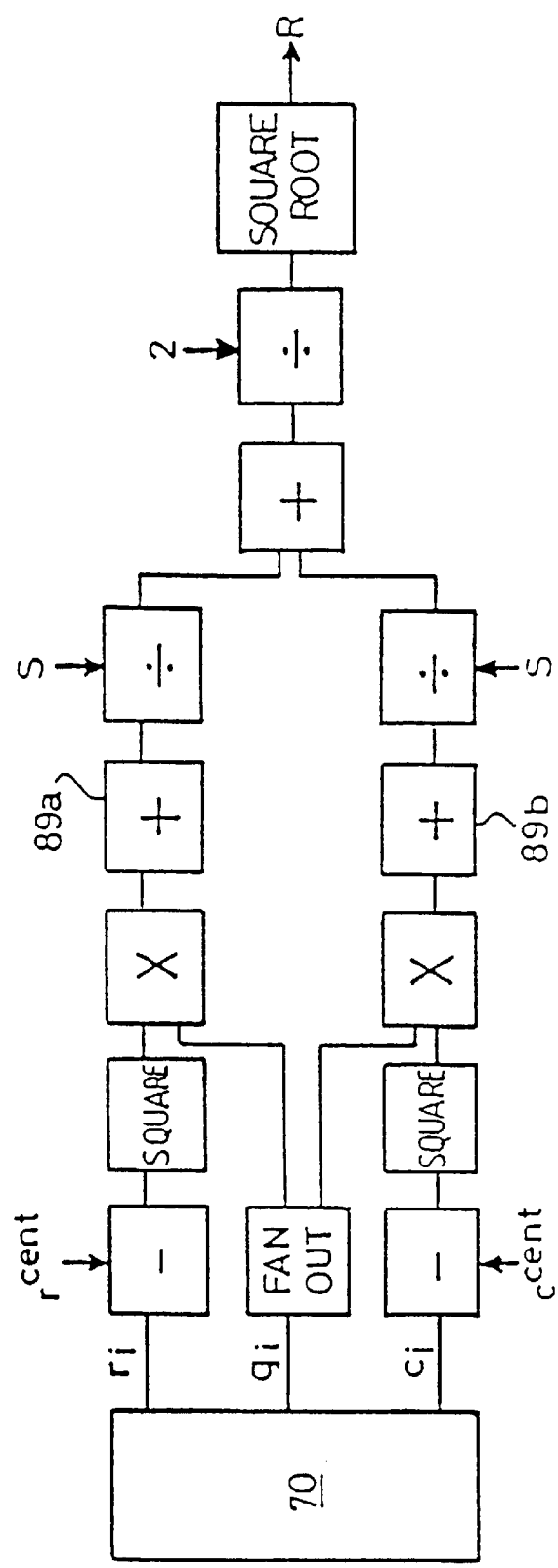
FIG. 6 is a similar schematic logic diagram indicating how a second order moment R can be calculated once the values of $r^{cent}$, $C^{cent}$, S and N are known, again on the assumption that a DSP is under software control and is simply forming a series of simple arithmetic functions.

FIG. 6 shows an implementation for calculation of radius R again using logic devices instead of a single programmed processor such as 44.

In this implementation, radius R, is calculated once $i^{cent}$, $c^{cent}$, N and S are known using the formulae given earlier in relation to FIGS. 3a and 3b, for $i^{cent}$, $c^{cent}$, and S.

The separate function boxes in FIG. 6 are not here described in detail since the nature and purpose of their individual functions, and how they interact, will be clear from their markings in FIG. 6.

Although not shown in FIG. 6, a buffer memory and feedback should follow each of the sum boxes 89a and 89b, as in FIG. 5.

The parameters calculated by the FIG. 5 circuit are fed in (for example via latches) at appropriate points.

Implementation

All the logic functions could be implemented as suitably programmed Texas DSP devices eg the TMS320C50. Algorithms for programming these chips and full details of interfacing associated memory (RAM) and input-output devices, are given in a series of technical manuals published by Texas Instruments, including:

TMS320C5X Users Guide 1993 (Part Number SPRU056B), and Digital Signal Processing Applications with the TMS320 Family (1989 part number SPRA012A).

An alternative implementation would be to use discrete logic chips, for example transistor to transistor (TTL) logic components.

Sample Presentation

As already mentioned FIGS. 1(*a*), 1(*b*) and 1(*c*) illustrate three different arrangements of sample and lens viewing systems. FIG. 1(*a*) is for a self luminous sample, FIGS. 1(*b*) and 1(*c*) show a sample excited by illumination so as to produce fluorescent emissions, in FIG. 1(*b*) by transillumination and in FIG. 1(*c*) by epi-illumination.

In each of these figures the fiber optic input 2 may be preceded by a demagnifying taper (not shown) of output diameter equal to the input diameter of the fibre optic window 2, as a means of achieving larger light gathering efficiency.

Figure 7A:
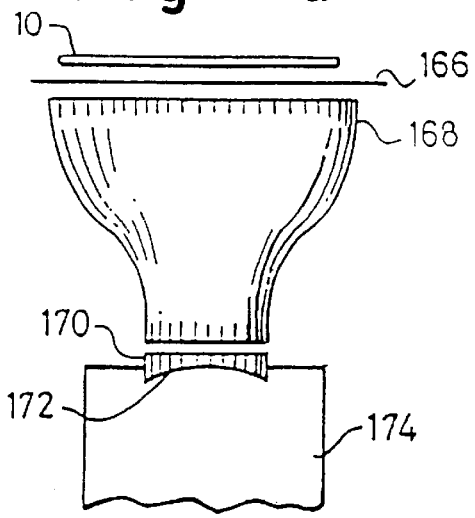
FIGS. 7(a), 7(b) and 7(c) show three preferred combinations of sample, and image intensifier.
Figure 7C:
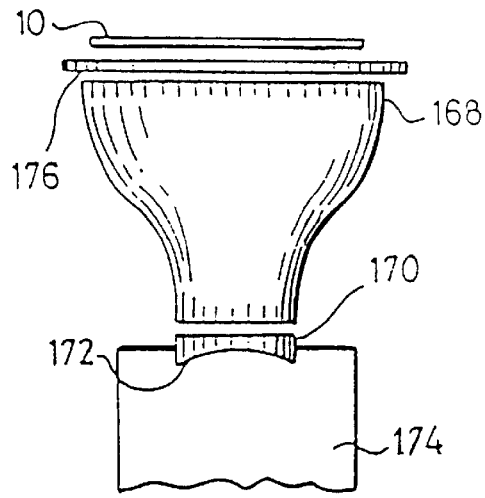
Figure 7B:
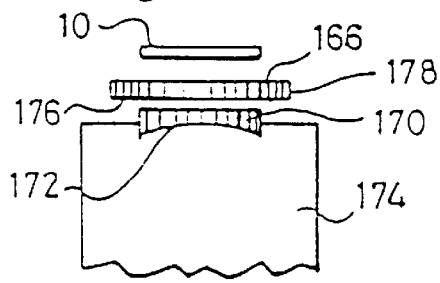

FIGS. 7a, 7b and 7c illustrate three different arrangements of the sample, and a fiber optic coupling plate.

In FIG. 7a the signal produced by sample 10, is incident on a tapered fiber optic plate 168. The plate 168 presents a large area commensurate with the sample area but tapers to a smaller area commensurate with that of the fiber optic input 170 to the photocathode 172 of the image intensifier. This demagnification permits the larger sample area to be viewed by the CCD camera 174 than would otherwise be the case. A thin optical filter 166 can be inserted between sample and input to the taper to select a wavelength range.

A reversal of the taper so that the larger area of the tapered fiber optic plate 168 is presented to the photocathode 172, allows for magnification of the sample area.

In another preferred embodiment as shown in FIG. 7B, a fiber optic coupling plate 176 made of optical fiber material or coated with a thin layer of optical filter material 166 is inserted between sample and fibre optic input 170. A flange 178 is provided around the edge of the plate 176 for ease of handling.

The plate 176 can be used separately with a tapered optical fiber plate 168 as shown in FIG. 7C.

Figure 8:
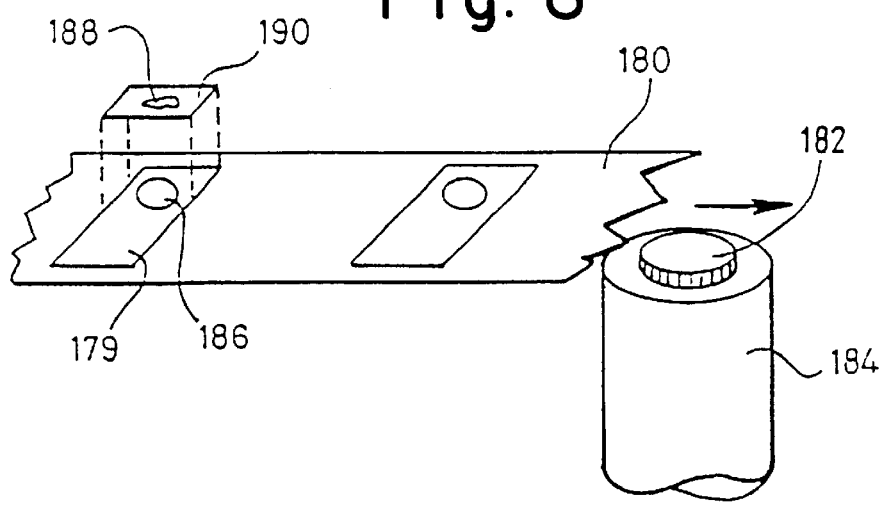
FIG. 8 shows how a system can be automated for measuring several samples.

FIG. 8 shows an automated system for presenting samples to be measured. The system comprises a number of cartridges 179 spaced apart along a feed conveyor 180 which passes directly above a fiber optic coupling plate 182 of an image intensifier 184. Each cartridge 179 consists of one or more optical filters 186 mounted in a support material onto which a sample 188, attached to the underside of 190, is placed. The cartridge may be indented to facilitate handling by an autofeeder. The sample 188 is then automatically scanned and the light emission therefrom mapped and stored as a series of coordinates possibly in combination with data indicative of the shape of the specimen containing the labelled producing the light emission. The sample is then indexed so that the next sample is presented for scanning and subsequent analysis and storage of coordinate data relating thereto.

Dark level and threshold correction

Normally the dark level response of each pixel is obtained from a measurement of the statistical distribution of counts in that pixel for a reasonable number of frames (for example 1000) in the absence of light or other radiation. The results of these measurements may be stored in the threshold store 74 (or a dedicated dark level correction signals store 137) and analysed using the host processor 44. A dark level look-up table can thus be created in the threshold store 74 (or store 137) by entering the mean value of the dark level response from each pixel defined by its address r and c. Likewise other look-up tables for each of the thresholds T1, T2 and T3 can be created and stored in 74 by adding appropriate offsets to the counts corresponding to the dark level value of any pixel, such offsets being based on measurements of statistical distributions of typical ion and other background events, and statistical distributions of light events from other sources, as required.

These offsets may be either constant across the field of view or allowed to vary with the pixel address r and c. Such variation of offsets with pixel address may be obtained by comparing the response as between pixels when the system is exposed to light emission sources which are uniform across the field of view.

Figure 9:
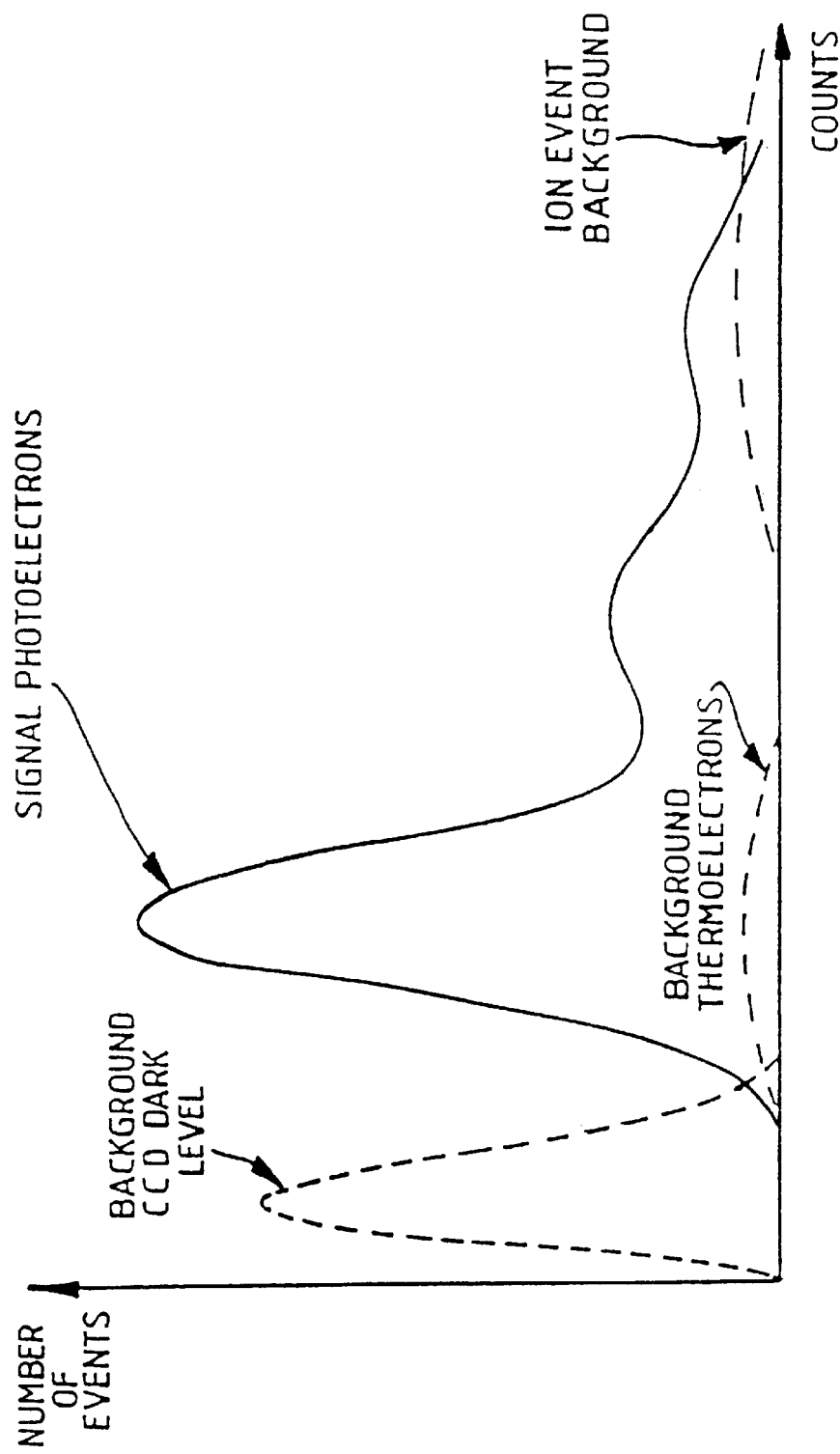
FIG. 9 illustrates graphically a typical distribution of "counts" associated with one pixel in a CCD array, for different events.

A typical distribution of photo energy/charge "counts" associated with one pixel in a CCD array such as described herein, for different types of event which can occur over a period of time, is shown in FIG. 9, which should be viewed in conjunction with FIG. 3(*c*).

What is claimed is:

1. A method of interrogating a charge pattern on a CCD array arising from the emission of photons of light by labeled material in a sample during an exposure period comprising the steps of:
   (1) organizing the addressing of the CCD so as to define sub-regions which make up the sensitive area of the array, the quantity of charge found in each sub-region at the end of the said exposure period being proportional to the photon energy incident thereon during the said period;
   (2) storing for each sub-region an electrical signal having a value indicative of the said charge for reading out as data signals;
   (3) reading out the stored electrical signals as date signals;
   (4) performing measurements of each individual data signal so as to identify and isolate from adjoining data signals any clusters of data signals of unlimited size and shape and which by their magnitude and adjacency are attributable to one or more photons of light impinging on a region of the array;
   (5) comparing the measurements with at least one threshold so as to distinguish clusters of data signal values attributable to photon emitting regions labeled material from the remaining regions of the sample;
   (6) computing the coordinates of the centroid of each cluster of data signal values which satisfies the thresholding criteria with reference to the sub-regions of the camera array, and
   (7) storing the centroid coordinates in a memory together with the centroid coordinates of any other threshold satisfying clusters of data signals identified during the same interrogation.

2. The method of claim 1 which includes the further step of storing the coordinates from each of a succession of interrogations of the same sample in an accumulation store to enable a list of the recorded light photon emissions and/or a display of the events, to be produced by reading out the store.

3. A method of interrogating a charge pattern on a CCD array arising from the emission of photons of light by labelled material in a sample during a succession of exposure periods comprising the steps of:
   (1) organizing the addressing of the CCD so as to define a plurality of regions in the CCD array, each of which is individually addressable,
   (2) repetitively scanning the CCD array of the camera, to interrogate the charge pattern on the array, each interrogation being preceded by an exposure period and followed by a resetting step, which initiates the beginning of the next following exposure period,
   (3) during each interrogation generating data signals whose values describe the charge pattern on the addressable regions in the array,
   (4) performing measurements on the data signals by comparing each with at least one threshold as to value, and a threshold as to proximity with other data signals whose values also satisfy the value threshold criteria, so as to identify and isolate from other signals arising during the interrogation clusters of data values all of which satisfy the threshold criteria and all of which are from neighbouring regions of the array as determined by the proximity criterion, thereby to identify genuine clusters of data values,
   (5) identifying a center position for each identified genuine cluster of such data values and storing the coordinates of the center position in a memory together with the centre coordinates of any other identified genuine clusters of data values occurring during the same interrogation, and
   (6) during subsequent interrogations of the CCD covering charge pattern, performing the same steps of data signal generation, performing measurements thereon using at least one threshold as to value and a threshold as to proximity, identifying a center position for each identified genuine cluster and storing the coordinates of the center position for each of the clusters identified during each of the interrogations associated with the said repetitive scanning.

4. The method of claim 3, wherein the data signal values generated for each interrogation are stored and subsequently read out by a computing and data processing means for performing the said measurements thereon.

5. The method of claim 3, wherein coordinates from each of a succession of interrogations of the same sample are stored in an accumulation store.

6. The method of claim 3, comprising the further step of reading out the stored coordinates and producing a list thereof.

7. The method of claim 3, comprising the further step of operating a visual display system so as to reproduce therein the scanned area of the CCD array and modulating the photon producing element of the display system so as to generate visually distinguishable features in the display at positions defined by the stored coordinates.

8. A method as claimed in claim 1, in which the distribution of a labelling material across a sample is analysed by computational analysis of electrical signals descriptive of the said distribution obtained from the said material, thereby to determine drug take-up by tissue and/or cells, or "DNA, RNA or protein" hybridization.

9. The method of claim 8 as applied to apparatus in which light from an image intensifier causes charge to be depleted over two or more neighbouring addressable regions of a CCD camera array, and in which the method includes the step of centroiding photon induced signals from a group of sub-regions of the CCD camera, identified as being linked to a single emission, so as to estimate the position in the sample of the point from which the light photon or photons have emanated, which caused the charge distribution concerned, and identifying that position as being the point of interest, and storing the coordinates of that position relative to the CCD array for subsequent mapping of labelling material relative to the sample.

10. A method as claimed claim 1, for determining the presence and position of two or more differently labelled materials in a sample comprising the step of labelling by means of materials giving off different wavelength light photons to enable the different substances to be identified by optical filtering the emitted light photons before they reach the CCD camera, whereby the presence of the two or more different materials in the sample is checked by identifying clusters and storing with each cluster not only the center coordinates but also an indication of the wavelength of the light producing the cluster by reference to the filter in use.

11. A method of determining the distribution of a first material in a base material, such as the distribution of a drug within organ tissue, comprising the steps of:

(1) labelling the first material with a light photon emitting substance, (2) exposing the base material to the first material (which may be in the form of a thin slice thereof), in a manner such that take-up of the first material by the base can be expected, and if not in the form of a thin slice removing from the said base material a thin slice thereof, after said exposure, (3) imaging the thin slice onto a CCD array, (4) establishing a uniform charge pattern on the CCD array at the beginning of each of a succession of exposure periods, at the end of each of which the array is interrogated, and the charge pattern thereon is read out before reinstating the uniform charge pattern, (5) converting the read-out electrical charge patterns into electrical signals having numerical values of the variation in charge over the array, (6) position-relating the electrical signals to the array, to permit the presence and position of sites of photon activity from the image intensifier (and therefore the position of a light photon emitting material in the sample area) to be identified from the said electrical signals, (7) determining from an analysis of the electrical signals, ion events occurring within the image intensifier and background noise events produced within the CCD array, and excluding therefrom signals relating to all such events, and (8) storing coordinates of points approximating to the center of each site for which electrical signals remain with reference to their position in the CCD array, as the coordinates of points from which one or more light photons has been emitted.

12. The method of claim 11, wherein the signals derived from the stored central point coordinates are used to control a visual display device for displaying the points in a two-dimensional display.

13. The method of claim 11, wherein the center points determined during each interrogation of the CCD array are accumulated in an accumulation store and the two-dimensional display is updated from the store on a regular basis so as to indicate all points for which photon activity is attributable from a given sample.

14. Apparatus adapted to interrogate a charge pattern on a CCD array such as may arise from the emission of photons of light by labelled material in a sample during an exposure period, comprising:

(1) means for addressing separately addressable sub-regions of the CCD array, (2) charge reading means adapted to investigate the charge in each sub-region during each interrogation of the CCD array to produce an electrical signal indicative of the photon emission activity to which each sub-region has been exposed during the preceding exposure period, (3) signal processing and computing means for performing measurements which determine one or more sub-region clusters each associated with a single photon emission event, first by identifying using a first threshold limitation a single charge-carrying sub-region and then by identifying using one or more further threshold limitations all charge-carrying sub-regions contiguously linked to the said single sub-region, whereby to identify each cluster regardless of its size and shape, (4) computing circuit means adapted to determine the coordinates of the center of each identified cluster of adjacent sub-regions, with reference to the sub-regions in the array, (5) memory means for storing signals relating to the center coordinates of each cluster of sub-regions, and (6) memory addressing means to read out from said memory means the coordinates of the centers of the identified clusters.

15. Apparatus as claimed in claim 14, wherein a fiber optic coupling plate which alters in cross-section from one face to the other is interposed between the sample and the CCD camera array to enhance the sensitivity.

16. Apparatus as claimed in claim 14, further comprising a scanning display system to which signals from the memory addressing means are supplied in synchronism with the scanning so as to produce in the display visually distinctive points at positions defined by the stored coordinate values so as to produce points in the display corresponding to the positions on which one or more light photons has impinged in the CCD array of a camera during the preceding exposure period.

17. Apparatus as claimed in claim 16, including means for updating the display on a regular basis, with information from subsequent memory addressing, whereby a picture is generated in the display indicating light photon emissions as they occur together with those which have already occurred.

18. Apparatus for detecting the presence and position of light photon emitting material in a sample, comprising:

(1) CCD camera means, (2) sample support means for the labelled sample, (3) means for repetitively scanning the array of the CCD camera, each scan corresponding to an interrogation of the array and being followed by a resetting step and preceded by an exposure step, (4) means for generating from the scanning data signals corresponding to the charge pattern found during each said interrogation of the CCD array, (5) signal processing and computing means for performing measurements which determine one or more sub-region clusters each associated with a single photon emission event, first by identifying using a first threshold limitation a single charge-carrying sub-region and then by identifying using one or more further threshold limitations all charge-carrying sub-regions contiguously linked to the said single sub-region, whereby to identify each cluster regardless of its size and shape, (6) means for computing from the data signals of each identified cluster the x, y coordinates of a center of the cluster, with reference to the scanned CCD array, and (7) memory means for storing at least the center coordinates of each cluster, identified during the same interrogation of the CCD array.

19. Apparatus as claimed in claim 18, further comprising means for reading out the data in the memory and producing a list of the center coordinates stored therein.

20. Apparatus as claimed in claim 18, also comprising a visual display system responsive to signals read out from the memory means thereby to reproduce in the visual display a reproduction of the scanned area of the CCD array, and means for utilizing the signals read out from the memory means to modulate the visual display so as to generate visually distinctive features in the display at positions defined by the coordinates stored in the memory.

21. Apparatus as claimed in claim 18, in which a non-inverted mode cooled CCD array is used, fitted with low noise readout circuits, to enable operation at higher read out rates which further reduces noise integration periods.

22. Apparatus as claimed in claim 20, wherein an image intensifier is employed ahead of the CCD to enable signals arising from single photon emissions to be handled.

23. Apparatus as claimed in claim 18, further comprising an addressable memory within which information is stored corresponding to the outline and detail of the sample and memory addressing means for reading out from the said memory signals in synchronism with a scanning display device, the signals read out from the memory being supplied to the scanning display device to produce in the display an image of the sample from which one or more photons of light has been detected by the CCD camera in combination with and superimposed thereon visually distinctive points corresponding in position to the coordinates stored in the first mentioned memory so that the superimposed points are in correct registry with the image of the sample from which one or more light photons has been detected to enable the regions of the sample from which one or more photons of light have arisen readily to be seen.

24. Apparatus as claimed in claim 14, wherein the camera includes a so-called first generation image intensifier.

25. Apparatus as claimed in claim 23, wherein the CCD camera is operated in "inverted mode" so that contributions to background from fluctuations in thermal noise in its CCD array, at room temperatures, can be reduced.

26. Apparatus as claimed in claim 25, wherein the said duration of each interrogation is shorter than the duration of the preceding exposure period.

27. Apparatus as claimed of claim 14, wherein the addressing of the CCD array is organized so as to define a plurality of sub-regions which together make up the optically sensitive region of the camera array, the quantity of photon energy incident on each sub-region during an exposure period determining the charge to be found on that sub-region during the following interrogation, so that an electrical signal indicative of the photon energy incident on each sub-region can be obtained and stored as an electrical information signal for each sub-region.

28. Apparatus as claimed in claim 14, wherein the CCD array is part of a cooled CCD camera.

29. Apparatus as claimed of claim 14, wherein for display purposes a photon producing element of a scanning display system is modulated by the said electrical information signal obtainable from the interrogation of the CCD array so as to generate a visual difference between one part of the display and another, depending on the level of photon activity on the corresponding sub-regions of the CCD array during the preceding exposure period.

30. Apparatus as claimed in claim 14, wherein a display system is modulated by signals obtained by repeatedly reading out the coordinate accumulation store so that, when referred to, the display will present a continually updated picture of the positions from which light photons have been detected in the sample.

31. Apparatus as claimed in claim 27, wherein a threshold is applied to the information signals so that in the simplest case the modulation is two-state and sub-regions which have received photon energy greater than a value for example K, are displayed in one color and all other sub-regions are displayed in a contrasting color.

32. Apparatus as claimed in claim 29, wherein the sub-region related information signals are employed to produce a list of coordinates at which events have occurred.

33. Apparatus as claimed in claim 14, wherein the sensitivity of the imaging system (and therefore overall signal processing and image analysing system) is enhanced by optically coupling the sample to the photocathode of the image intensifier by means of a fiber optic coupling plate.

34. Apparatus as claimed in claim 33, wherein the coupling plate alters in cross-section from one face to the other.

35. A method of interrogating a charge pattern on a CCD array arising from the emission of photons of light by labelled material in a sample during an exposure period comprising the steps of:

(1) organizing the addressing of the CCD so as to define sub-regions which make up the sensitive area of the array, the quantity of charge found in each sub-region at the end of the said exposure period being proportional to the photon energy incident thereon during the said period;

(2) storing for each sub-region an electrical signal having a value indicative of the said charge for reading out as data signals;

(3) reading out the stored electrical signals as data signals;

(4) performing measurements on the data signals so as to identify any clusters of data values from adjacent sub-regions, attributable to one or more photons of light impinging thereon;

(5) comparing the measurements with at least one threshold so as to distinguish clusters attributable to photon emitting regions of labelled material from the remainder of the sample;

(6) computing the coordinates of the centroid of each cluster of data values so produced with reference to the sub-regions of the camera array, and (7) storing the centroid coordinates in a memory together with the centroid coordinates of any other clusters identified during the same interrogation.

36. A method of interrogating a charge pattern on a CCD array arising from the emission of photons of light by labelled material in a sample during a succession of exposure periods comprising the steps of:

(1) organising the addressing of the CCD so as to define a plurality of regions in the CCD array, each of which is individually addressable;

(2) repetitively scanning the CCD array of the camera, to interrogate the charge pattern on the array, each interrogation being preceded by an exposure period and followed by a resetting step, which initiates the beginning of the next following exposure period, (3) during each interrogation generating data signals whose values describe the charge pattern on the addressable regions in the array, (4) performing measurements on the data signals by comparing each with at least one threshold as to value, and a threshold as to proximity with other signals whose values also satisfy the value threshold criteria, so as to identify clusters of data values all of which satisfy the threshold value and all of which are from neighbouring regions of the array as determined by the proximity criterion, thereby to identify genuine clusters of data values, (5) identifying a center position for each identified cluster of such data values and storing the coordinates of the centre position in a memory together with the center coordinates of any other identified clusters occurring during the same interrogation, and (6) performing the same steps of interrogation, generation of data signals, performing measurements thereon using a threshold as to value and a threshold as to proximity with other signals which also satisfy the value threshold criterion, and identifying a center position for each identified cluster and storing the coordinates of the center position for each of the interrogations associated with the said repetitive scanning.

37. A method of interrogating a charge pattern on a CCD array arising from the emission of photons of light by labeled material in a sample during an exposure period comprising the steps of:

(1) organizing the addressing of the CCD so as to define sub-regions which make up the sensitive area of the array, the quantity of charge found in each sub-region at the end of the said exposure period being proportional to the photon energy incident thereon during the said period;

(2) storing for each sub-region an electrical signal having a value indicative of the said charge for reading out as data signals;

(3) reading out the stored electrical signals as data signals;

(4) performing measurements on each individual data signal so as first to identify a single pixel having a charge exceeding a threshold, then identify all adjoining pixels having a charge exceeding a second threshold and the identifying pixels adjacent the adjoining pixels having a charge exceeding the second threshold, and so on iteratively until as more pixels having a charge value exceeding the second threshold can be added, whereby to identify and isolate from adjoining data signals arising due to any clusters of pixels which by their magnitude and adjacency are attributable to one or more photons of light impinging on a region of the array;

(5) computing the coordinates of the centroid of each cluster of pixel charge values which satisfies the thresholding criteria with reference to the sub-regions of the camera array, and (6) storing the centroid coordinates in a memory together with the centroid coordinates of any other threshold satisfying clusters of pixels identified during the same interrogation.

\* \* \* \* \*